(12) United States Patent
Fujisawa et al.

(10) Patent No.: US 10,309,895 B2
(45) Date of Patent: Jun. 4, 2019

(54) ELECTROMAGNETIC WAVE DETECTOR AND GAS ANALYSIS DEVICE HAVING DUAL ELECTROMAGNETIC WAVE SENSORS FOR DETECTING ONE OF LIGHT IN A PREDETERMINED WAVELENGTH BAND AND PREDETERMINED POLARIZATION

(71) Applicant: MITSUBISHI ELECTRIC CORPORATION, Chiyoda-ku (JP)

(72) Inventors: Daisuke Fujisawa, Chiyoda-ku (JP); Shimpei Ogawa, Chiyoda-ku (JP)

(73) Assignee: MITSUBISHI ELECTRIC CORPORATION, Chiyoda-ku (JP)

( * ) Notice: Subject to any disclaimer, the term of this patent is extended or adjusted under 35 U.S.C. 154(b) by 133 days.

(21) Appl. No.: 15/543,421

(22) PCT Filed: Jan. 4, 2016

(86) PCT No.: PCT/JP2016/050027
§ 371 (c)(1),
(2) Date: Jul. 13, 2017

(87) PCT Pub. No.: WO2016/129293
PCT Pub. Date: Aug. 18, 2016

(65) Prior Publication Data
US 2018/0003622 A1    Jan. 4, 2018

(30) Foreign Application Priority Data
Feb. 9, 2015  (JP) ................................ 2015-022886

(51) Int. Cl.
*G01N 21/3504*     (2014.01)
*G01N 21/31*       (2006.01)
(Continued)

(52) U.S. Cl.
CPC .......... *G01N 21/314* (2013.01); *G01J 5/0225* (2013.01); *G01J 5/0862* (2013.01);
(Continued)

(58) Field of Classification Search
CPC .. G01N 21/21; G01N 21/314; G01N 21/3504; G01N 33/4927; H01L 35/32
(Continued)

(56) References Cited

U.S. PATENT DOCUMENTS

| | | | |
|---|---|---|---|
| 2,898,800 A * | 8/1959 | Bergson | G01N 21/314 250/214.1 |
| 2002/0040967 A1 | 4/2002 | Oda | |
| 2012/0228506 A1 | 9/2012 | Honda et al. | |
| 2012/0235038 A1 | 9/2012 | Nishikawa et al. | |
| 2014/0264029 A1 | 9/2014 | Tomioka | |

FOREIGN PATENT DOCUMENTS

| | | |
|---|---|---|
| JP | 11-258040 A | 9/1999 |
| JP | 2002-071452 A | 3/2002 |

(Continued)

OTHER PUBLICATIONS

International Preliminary Report on Patentability and Written Opinion dated Aug. 24, 2017 in PCT/JP2016/050027.
(Continued)

*Primary Examiner* — Que Tan Le
(74) *Attorney, Agent, or Firm* — Oblon, McClelland, Maier & Neustadt, L.L.P.

(57) ABSTRACT

An electromagnetic wave detector including a first electromagnetic wave sensor including a light reception unit held in midair above a substrate by a support leg and a second electromagnetic wave sensor including a light reception unit held in midair above the substrate by a support leg having same structure as the support leg of the first electromagnetic wave sensor and provided adjacent to the first electromagnetic wave sensor. The light reception unit of the first electromagnetic wave sensor includes a reflective film, the
(Continued)

light reception unit of the second electromagnetic wave sensor includes an electromagnetic wave absorption body for detecting light of a prescribed wavelength band or a prescribed polarization, and the difference between the output of the second electromagnetic wave sensor and the first electromagnetic wave sensor is output.

19 Claims, 12 Drawing Sheets

(51) Int. Cl.
  G01N 21/41 (2006.01)
  G01N 21/21 (2006.01)
  G01N 33/497 (2006.01)
  G01J 5/08 (2006.01)
  G01J 5/02 (2006.01)
(52) U.S. Cl.
  CPC ......... *G01N 21/21* (2013.01); *G01N 21/3504* (2013.01); *G01N 21/41* (2013.01); *G01N 33/4972* (2013.01)
(58) Field of Classification Search
  USPC .................................................. 250/222.2
  See application file for complete search history.

(56) References Cited

FOREIGN PATENT DOCUMENTS

| | | |
|---|---|---|
| JP | 2005-172762 A | 6/2005 |
| JP | 2010-507082 A | 3/2010 |
| JP | 2011-027699 A | 2/2011 |
| JP | 2011-095137 A | 5/2011 |
| JP | 2012-189357 A | 10/2012 |
| JP | 2013-195148 A | 9/2013 |
| JP | 2014-032068 A | 2/2014 |
| JP | 2014-081261 A | 5/2014 |
| JP | 2014-163674 A | 9/2014 |
| WO | 2008/046659 A1 | 4/2008 |

OTHER PUBLICATIONS

Japanese Office Action dated Jun. 7, 2016 in Japanese Patent Application No. 2016-524157 (with partial English translation).
Japanese Office Action dated Sep. 27, 2016 in Japanese Patent Application No. 2016-524157 (with partial English translation).
International Search Report dated Mar. 15, 2016 in PCT/JP2016/050027, filed on Jan. 4, 2016.
Office Action dated Sep. 20, 2018 in Chinese Patent Application No. 201680007199.8 (with unedited computer generated English translation), 8 pages.

\* cited by examiner

I-I CROSS SECTION (a)

II-II CROSS SECTION (b)

IV-IV CROSS SECTION

V-V CROSS SECTION (a)

(b)

(a)

(b)

(a)

(b)

(a)

(b)

(c)

A-A CROSS SECTION

B-B CROSS SECTION

C-C CROSS SECTION

C-C CROSS SECTION

D-D CROSS SECTION

E-E CROSS SECTION

ELECTROMAGNETIC WAVE DETECTOR AND GAS ANALYSIS DEVICE HAVING DUAL ELECTROMAGNETIC WAVE SENSORS FOR DETECTING ONE OF LIGHT IN A PREDETERMINED WAVELENGTH BAND AND PREDETERMINED POLARIZATION

TECHNICAL FIELD

The present invention relates to an electromagnetic wave detector which detects an electromagnetic wave in a specific wavelength range by converting the electromagnetic wave into heat, and to a gas analysis device including the electromagnetic wave detector.

RELATED ART

Home appliances and the like need to include sensitive and simple electromagnetic wave detectors each of which detects the position of a human body or temperature distribution in a room in order to realize power saving and a comfortable space. As such an electromagnetic wave detector, an electromagnetic wave sensor in which a thermopile is used in a pixel is conventionally used. In the electromagnetic wave sensor, a hot junction of a thermocouple is provided above a cavity and a cold junction is provided on a frame body, and a temperature of the hot junction can be known from a thermoelectromotive force generated according to the difference in temperature between the hot junction and the cold junction. In addition, sensitivity of the electromagnetic wave sensor is improved by reducing thermal capacity of the hot junction, suppressing thermal conductivity from the hot junction to the cold junction, increasing absorption by an electromagnetic-wave absorbing film (see Patent Document 1).

PRIOR ART DOCUMENT

Patent Document

Patent Document 1: JP 2005-172762 A

SUMMARY OF THE INVENTION

Problems to be Solved by the Invention

In a case where a wavelength of an electromagnetic wave to be detected is selected in a conventional electromagnetic wave detector, formation of an electromagnetic-wave absorbing film which absorbs an electromagnetic wave in a predetermined wavelength band in a light reception unit (temperature sensor unit) enables an electromagnetic wave sensor to have wavelength selectivity in sensitivity. In a case where an electromagnetic wave absorption unit is made of a thermopile, however, in addition to electromagnetic wave absorption at a hot junction of a thermocouple, electromagnetic wave absorption occurs at a support leg portion (for example, wiring or the thermocouple) which holds the light reception unit in midair. Sensor output caused by electromagnetic wave absorption at the support leg portion deteriorates wavelength selectivity in the electromagnetic-wave sensitivity.

The present invention is made in order to solve the above problem. An object of the present invention is to provide a gas analysis device which includes an electromagnetic wave detector improved in wavelength selectivity in electromagnetic-wave sensitivity.

Means for Solving the Problems

An electromagnetic wave detector according to the present invention includes a substrate, a first electromagnetic wave sensor which includes a light reception unit held in midair above the substrate by a support leg, and a second electromagnetic wave sensor which includes a light reception unit held in midair above the substrate by a support leg having a structure identical to that of the support leg of the first electromagnetic wave sensor, the second electromagnetic wave sensor being provided to be adjacent to the first electromagnetic wave sensor. The light reception unit of the first electromagnetic wave sensor includes a flat reflective film covering the entire surface of the light reception unit. The light reception unit of the second electromagnetic wave sensor includes an electromagnetic wave absorption body which detects light in a predetermined wavelength band or light of a predetermined polarization. The electromagnetic wave detector outputs a difference in output between the second electromagnetic wave sensor and the first electromagnetic wave sensor.

Effects of the Invention

Since the electromagnetic wave detector according to the present invention has the above configuration, sensor output caused by electromagnetic wave absorption at the support leg portion which holds the light reception unit in midair can be subtracted. Therefore, wavelength selectivity in electromagnetic-wave sensitivity is improved.

EMBODIMENTS OF THE INVENTION

First Embodiment

In the embodiments of the present invention, a description will be given of a case where a visible light detector or an infrared light detector is used as an electromagnetic wave detector. However, the present invention is effectively applied to a detector for a region of an ultraviolet light, a near-infrared light, a terahertz (THz) wave, a radio wave such as a microwave, or the like, in addition to the above detectors. Note that in the embodiments according to the present invention, these types of light and radio waves are collectively referred to as electromagnetic waves.

Hereinafter, electromagnetic wave detectors according to the embodiments of the present invention will be described with reference to the drawings. In the embodiments, identical reference symbols are given to identical configurations, and a description of them will not be repeated.

Figure 1:
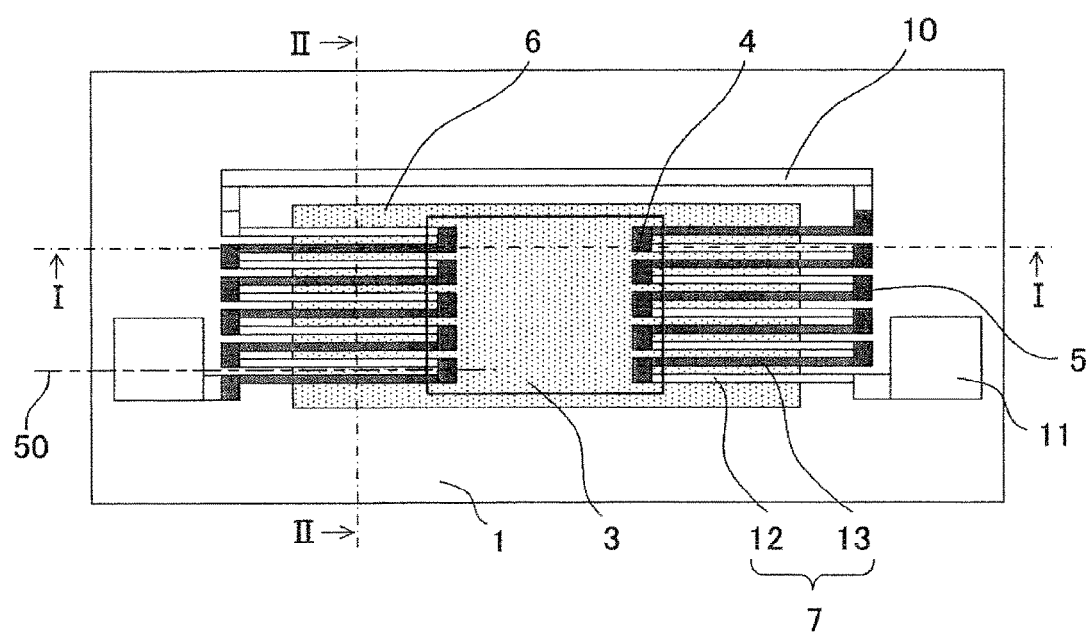
FIG. 1 is a top view of an electromagnetic wave sensor according to a first embodiment of the present invention.

First, as an underlying technique, an electromagnetic wave sensor which included in the electromagnetic wave detector according to the present invention will be described. FIG. 1 is a top view of an electromagnetic wave sensor 110, which is based on the underlying technique of the present invention. FIGS. 2(a) and 2(b) are cross-sectional views of the electromagnetic wave sensor 110. FIG. 2A is the cross-sectional view taken along line I-I in FIG. 1, and FIG. 2B is the cross-sectional view taken along line II-II in FIG. 1. Note that for the sake of easy understanding, an insulating film 2 on a substrate 1 is not illustrated in FIG. 1, and an electromagnetic wave absorption body 3 provided on hot junctions 4 is illustrated in a see-through state.

Figure 2:
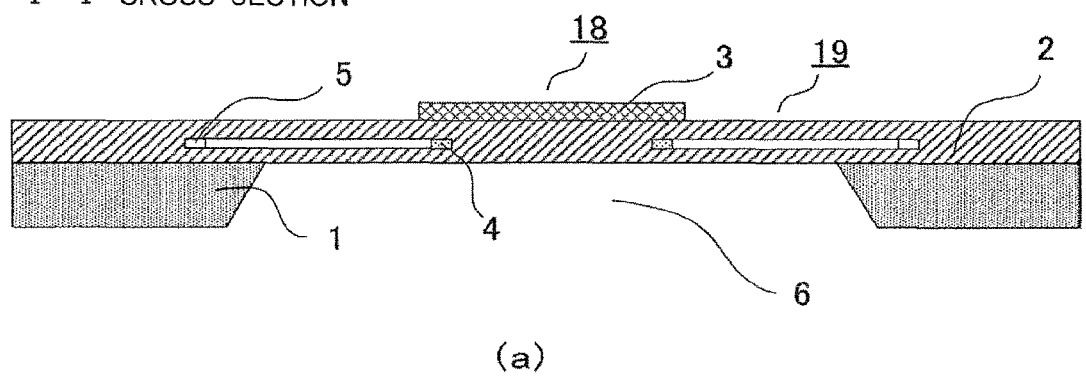
FIG. 2(a) is a cross-sectional view taken along line I-I in FIG. 1.
FIG. 2(b) is a cross-sectional view taken along line in FIG. 1.
Figure 2:
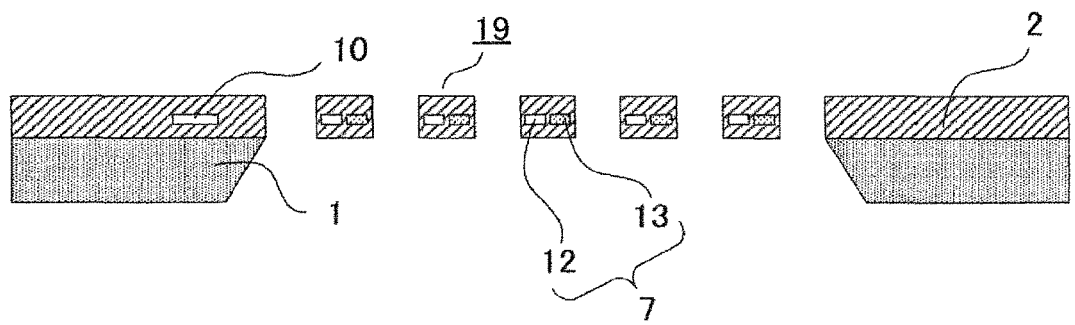

As illustrated in FIGS. 1 and 2, the electromagnetic wave sensor 110 includes a substrate 1 made of silicon or the like, a light reception unit 18 which detects an electromagnetic wave by converting the electromagnetic wave into heat, and a support leg (for example, wiring or a thermocouple) 19 which holds the light reception unit (temperature sensor unit) 18 in midair above the substrate 1. An insulating film 2 made of SiO$_2$, SiN, or the like is provided on the surface of the substrate 1. A thermopile device that includes a large number of thermocouples connected in series in order to increase output voltage) 7 including a plurality of thermocouples is provided on the insulating film 2. The insulating film 2 and the thermopile 7 (thermocouples) in the insulating film 2 are collectively referred to as the support leg 19. The support leg 19 has the effect of thermally insulating the light reception unit 18 by holding and floating the light reception unit 18 in midair.

As illustrated in FIGS. 1 and 2, the thermocouple is made of a pair of a thermocouple material a12 and a thermocouple material b13. For example, an aluminum film may be used as the thermocouple material a12, and a polysilicon film may be used as the thermocouple material b13. The thermocouple material a12 and the thermocouple material b13 are symmetrically arranged with respect to a central axis 50. One ends of the thermocouple material a12 and the thermocouple material b13 are connected to each other near the central axis 50 to form the hot junction 4. On the hot junctions 4, that is, on the side where an electromagnetic wave enters, the light reception unit 18 which includes the electromagnetic wave absorption body 3 that absorbs an electromagnetic wave in a predetermined wavelength range is provided. The electromagnetic wave absorption body 3 is provided to cover the hot junctions 4. The insulating film 2 and the electromagnetic wave absorption body 3 on the insulating film 2 are collectively referred to as the light reception unit 18. Note that since the electromagnetic wave absorption body 3 is not provided on the support leg 19, the surface of the support leg 19 is exposed to an electromagnetic wave.

The portion of the substrate 1 located under the light reception unit 18 is removed to form a cavity 6. In other words, the electromagnetic wave sensor 110 has a hollow structure in which the light reception unit 18 is held above the cavity 6 by the support leg 19. As described, provision of the cavity 6 under the light reception unit 18 prevents heat from escaping from the electromagnetic wave absorption body 3 and the thermopile 7 to the substrate 1.

In contrast, the other ends of the thermocouple material a12 and the thermocouple material b13 are connected to each other on the substrate 1 outside the cavity 6 to form a cold junction 5. That is, the cold junction 5 is provided in a region on the substrate 1 where the cavity 6 is not formed.

The thermocouples formed at distant locations on the substrate 1 are connected to each other via wiring 10.

In the electromagnetic wave sensor 110, the electromagnetic wave absorption body 3 absorbs an electromagnetic wave, and thus a temperature of the hot junction 4 increases, a difference in temperature occurs between the hot junction 4 and the cold junction 5, and an electromotive force is generated due to the Seebeck effect. By detecting the electromotive force from an output pad 11 via the wiring 10, an electromagnetic wave with a predetermined wavelength incident on the electromagnetic wave absorption body 3 can be detected.

Figure 3:
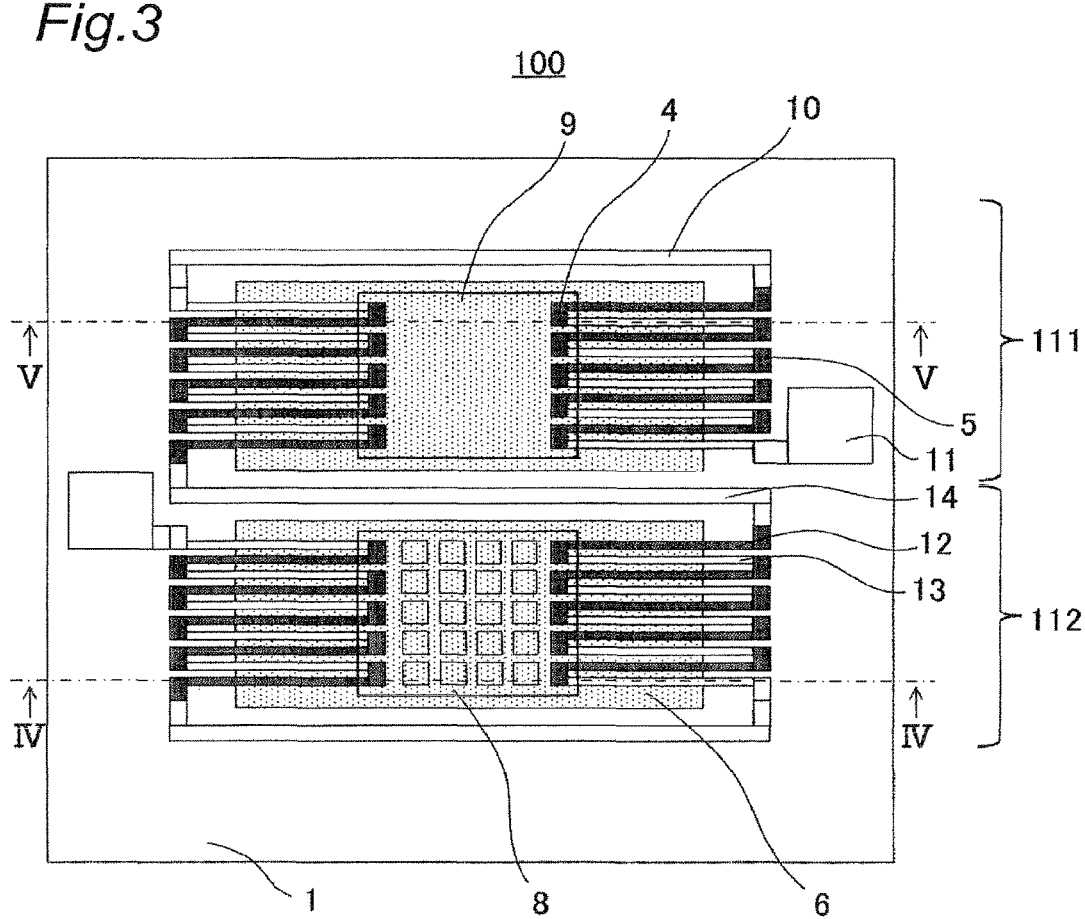
FIG. 3 is a top view of an electromagnetic wave detector according to the first embodiment of the present invention.
Figure 4:
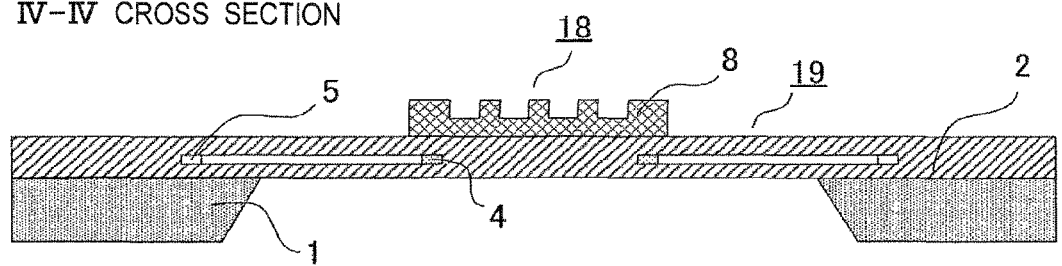
FIG. 4 is a cross-sectional view taken along line IV-IV in FIG. 3.
Figure 5:
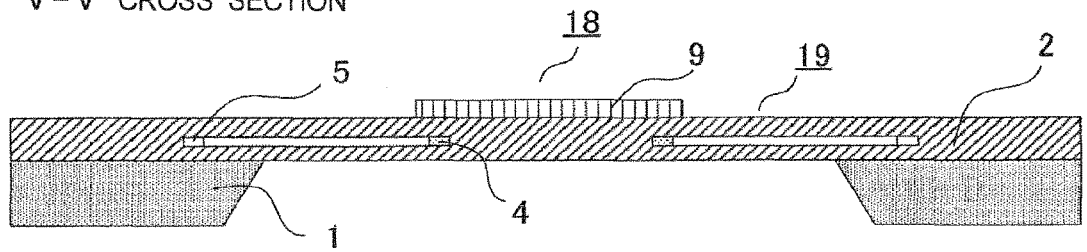
FIG. 5 is a cross-sectional view taken along line V-V in FIG. 3.

Next, the configuration of an electromagnetic wave detector 100 according to the first embodiment of the present invention will be described. The electromagnetic wave detector 100 includes two electromagnetic wave sensors described as the underlying technique. The configuration of a light reception unit 18 differs between the two electromagnetic wave sensors 111 and 112. FIG. 3 is a top view of the electromagnetic wave detector 100 according to the first embodiment of the present invention. FIG. 4 is a cross-sectional view taken along line IV-IV in FIG. 3. FIG. 5 is a cross-sectional view taken along line V-V in FIG. 3. Similarly to FIG. 1, in FIG. 3, for the sake of easy understanding, an insulating film 2 on a substrate 1 is not illustrated, and an electromagnetic wave absorption body 8 and a reflective film 9 provided on hot junctions 4 are illustrated in a see-through state.

The electromagnetic wave detector 100 includes the first electromagnetic wave sensor 111 and the second electromagnetic wave sensor 112 arranged to be adjacent to each other on the substrate 1. The first electromagnetic wave sensor 111 and the second electromagnetic wave sensor 112 are connected to each other via wiring 14.

The light reception unit 18 of the first electromagnetic wave sensor 111 includes the reflective film 9, and the reflective film 9 is provided to cover hot junctions 4 of thermocouples provided on the insulating film 2. In addition, the light reception unit 18 of the second electromagnetic wave sensor 112 includes the electromagnetic wave absorption body 8 which detects light in a predetermined wavelength band, and the electromagnetic wave absorption body 8 is provided to cover the hot junctions 4. The structures of the first electromagnetic wave sensor 111 and the second electromagnetic wave sensor 112 other than the above are similar to the structure of the electromagnetic wave sensor 110 described as the underlying technique with reference to FIGS. 1 and 2. In addition, a support leg 19 of the first electromagnetic wave sensor 111 and a support leg 19 of the second electromagnetic wave sensor 112 have identical structures.

As illustrated in FIG. 4, the electromagnetic wave absorption body 8 of the second electromagnetic wave sensor 112 has a periodic structure arranged in an array on the surface of the electromagnetic wave absorption body 8, such that surface plasmons which couple incident light with a specific wavelength to the surface are induced. The electromagnetic wave absorption body 8 is configured such that the absorbed amount of incident light with the specific wavelength is greater than the absorbed amount of incident light with a wavelength other than the specific wavelength. The electromagnetic wave absorption body 8 of the second electromagnetic wave sensor 112 is made of a metal such as Au or Ag. The thickness of the metal may be any as long as an incident electromagnetic wave does not penetrate through the metal. To get a rough idea of the thickness, it may be considered to be at least twice the depth of penetration at a target wavelength. In an electromagnetic wavelength band, the film thickness of the electromagnetic wave absorption body 8 is in a range from about several tens of nm to about several hundreds of nm. The structure of the electromagnetic wave absorption body 8 may be a structure where the surface of the electromagnetic wave absorption body 8 is covered with a metal which causes surface plasmons and periodic recesses and projections are arranged one-dimensionally or two-dimensionally. In this case, an absorption wavelength is determined depending on the cycle of the recesses and the projections. In addition, the structure of the electromagnetic wave absorption body 8 may be a structure where an insulating layer made of silicon oxide or the like is formed on a flat metal and a periodic isolated metal pattern is provided one-dimensionally or two-dimensionally on the insulating layer. In this case, the absorption wavelength is determined depending on the size of the isolated metal pattern.

In a case where surface plasmons are used for detection of an electromagnetic wave, Au, Ag, Al, or the like is preferably used as a metal material of the electromagnetic wave absorption body 8. In the present invention, effects called surface plasmons, pseudo surface plasmons, and a metamaterial are collectively referred to as "surface plasmons" since they are identical from the viewpoint of a wavelength selection effect caused by a periodic structure of a metal.

In addition, the electromagnetic wave absorption body 8 may have a single-layer structure of a metal film, a multi-layer film structure of a metal film and a dielectric, or a structure where an absorption wavelength is controlled by a multilayer film of a dielectric, or may have a structure where an absorption wavelength is controlled by changing the material included in the electromagnetic wave absorption body 8.

The reflective film 9 is made of a metal having a flat surface and high reflectivity in an electromagnetic wavelength band, such as Au, Ag, or Al.

The wiring 14 connects a cold junction 5 of a thermocouple material a12 of the first electromagnetic wave sensor 111 and a cold junction 5 of a thermocouple material a12 of the second electromagnetic wave sensor 112. Hereinafter, operation in a case where the cold junctions 5 are connected to each other as described above will be described.

Figure 6:
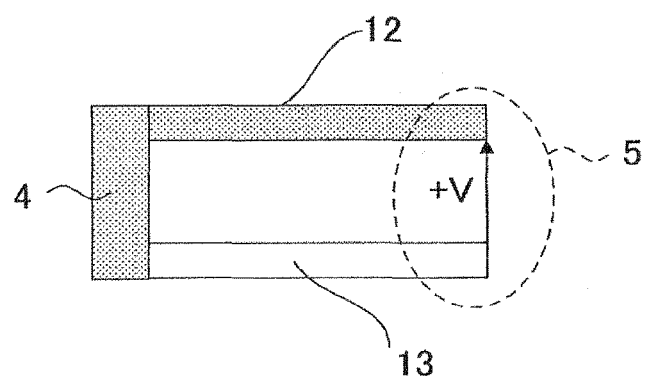
FIG. 6 is a schematic view for illustrating connection between thermocouples according to the first embodiment of the present invention.
Figure 6:
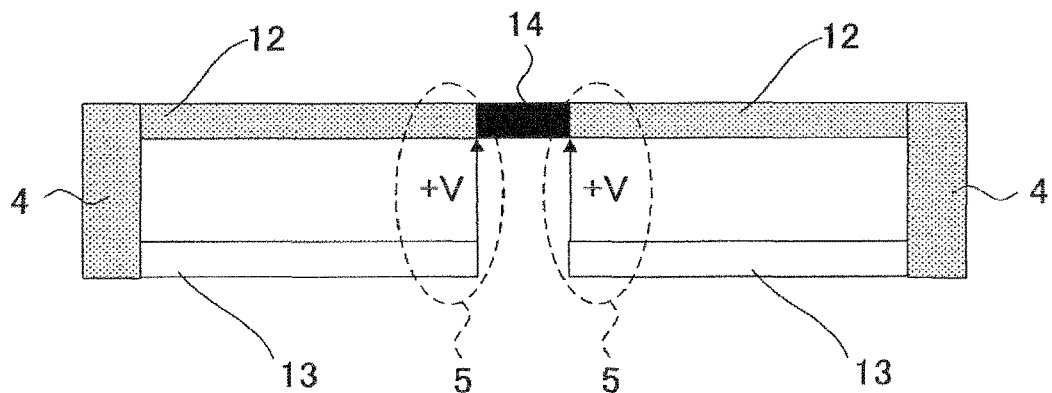

For the sake of simplicity, a description will be given using a thermocouple described in FIG. 6. FIG. 6(a) is a schematic view illustrating a principle of the thermocouple. FIG. 6(b) is a schematic view illustrating a state where two thermocouples are connected similarly to the thermocouples in the electromagnetic wave detector 100 according to the present embodiment. As illustrated in FIG. 6(a), in the thermocouple, an electromotive force V is generated due to a difference in temperature between a hot junction 4 and a cold junction 5. Next, as illustrated in FIG. 6(b), a case where identical thermocouple materials a12 are connected to each other via wiring 14 will be considered. In this case, since voltages are generated in opposite directions in the right and left thermocouples, when the voltage between thermocouple materials b13 of the right and left thermocouples is measured in a state where the thermocouple materials a12 are connected, the difference in voltage between the both thermocouples is calculated and is output. In a case where the temperature of the hot junctions 4 is equal to the temperature of the cold junctions 5, difference output is zero. Even in a case where a plurality of thermocouple materials a12 and thermocouple materials b13 are connected in series as in the electromagnetic wave detector 100 according to the present embodiment, a connection method for outputting the difference is basically the same as that illustrated in FIG. 6(b). By connecting output of the first electromagnetic wave sensor 111 and output of the second electromagnetic wave sensor 112 as illustrated in FIG. 6B, the difference in output between the both sensors is output. That is, the value obtained by subtracting the output of the first electromagnetic wave sensor 111 from the output of the second electromagnetic wave sensor 112 is output.

Figure 7:
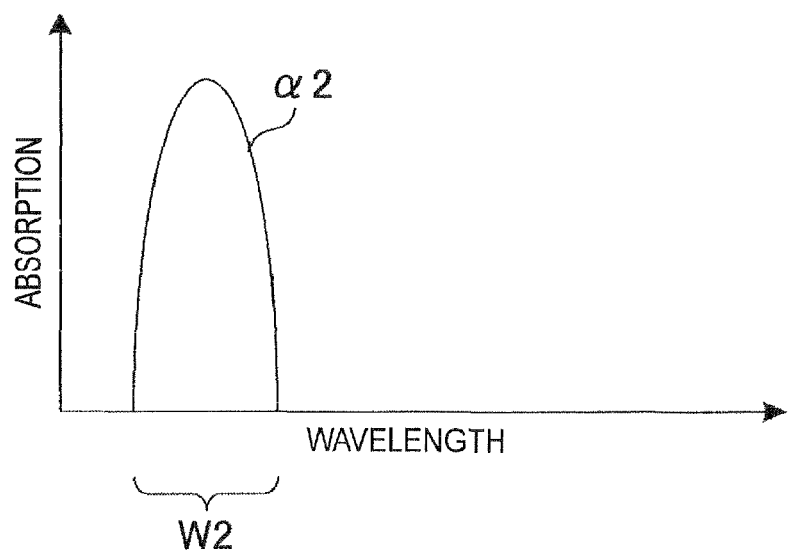
FIG. 7 is a schematic diagram for illustrating absorption characteristics of the electromagnetic wave detector.
Figure 7:
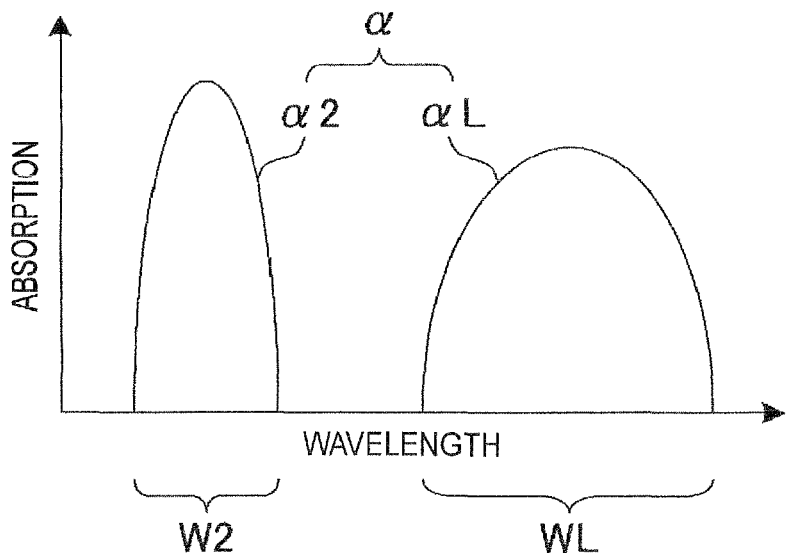

Next, effects of the electromagnetic wave detector 100 according to the first embodiment of the present invention will be described. FIG. 7(a) illustrates an ideal absorption characteristic in an electromagnetic wave sensor in which an electromagnetic wave absorption body 8 that absorbs light in a predetermined wavelength band is formed in order to achieve wavelength selectivity in sensitivity. FIG. 7(b) illustrates absorption characteristics of the second electromagnetic wave sensor 112 of the electromagnetic wave detector 100 according the first embodiment.

As illustrated in FIG. 7(a), in a case of the electromagnetic wave sensor including the electromagnetic wave absorption body 8 which absorbs an electromagnetic wave in a wavelength range W2, ideally, sensor output is obtained only from absorption α2 by the electromagnetic wave absorption body 8. However, as illustrated in FIG. 7B, in an actual sensor, the entire absorption α is a total of the absorption α2 by the electromagnetic wave absorption body 8 in the wavelength range W2 and absorption αL by the support leg 19 in a wavelength range WL. That is, output caused by absorption αL by the support leg 19 in the wavelength range WL is included in actual sensor output.

For example, in a case where the insulating film 2 is made of SiO$_2$ or SiN, the material itself absorbs light with a wavelength about 10 µm, and this absorption is reflected in output of the sensor. In a conventional thermopile, absorption by a support leg itself does not become a problem. However, it is revealed here that absorption intrinsic to the material of the support leg itself deteriorates wavelength selectivity and becomes a serious problem in order to realize a detector having wavelength selectivity as in the present invention.

In contrast, the electromagnetic wave detector 100 according to the present embodiment includes the first electromagnetic wave sensor 111 including the reflective film provided on the hot junctions 4, and the second electromagnetic wave sensor 112 including the electromagnetic wave absorption body 8 which is provided on the hot junctions 4 and absorbs light in a predetermined wavelength range. The first electromagnetic wave sensor 111 and the second electromagnetic wave sensor 112 are electrically connected to each other such that sensor output (thermoelectromotive force) of the first electromagnetic wave sensor 111 is subtracted from the sensor output (thermoelectromotive force) of the second electromagnetic wave sensor 112, and a signal is read from an output pad 11. Thus, the electromagnetic wave detector 100 which enables ideal sensor output not including absorption of an electromagnetic wave by the support leg 19 can be realized.

In particular, in the electromagnetic wave detector 100 according to the present embodiment, since the support leg of the first electromagnetic wave sensor 111 and the support leg of the second electromagnetic wave sensor 112 have identical structures, it is possible to eliminate an influence of the electromagnetic wave absorbed by the support leg 19 on sensor output by subtracting sensor output of the first electromagnetic wave sensor 111 from sensor output of the second electromagnetic wave sensor 112.

As described, the electromagnetic wave detector 100 according to the present embodiment includes the first electromagnetic wave sensor 111 which includes the light reception unit 18 held in midair above the substrate 1 by the support leg 19, and the second electromagnetic wave sensor 112 which includes the light reception unit 18 held in midair above the substrate 1 by the support leg 19 having the structure identical to that of the support leg 19 of the first electromagnetic wave sensor 111, the second electromagnetic wave sensor 112 being provided to be adjacent to the first electromagnetic wave sensor 111. The light reception unit 18 of the first electromagnetic wave sensor 111 includes the reflective film 9. The light reception unit 18 of the second electromagnetic wave sensor 112 includes the electromagnetic wave absorption body 8 which detects light in a predetermined wavelength band or light of a predetermined polarization. The difference in output between the second electromagnetic wave sensor 112 and the first electromagnetic wave sensor 111 is output.

Thus, sensor output caused by electromagnetic wave absorption by the support leg 19 which holds the light reception unit 18 in midair can be subtracted from output of the second electromagnetic wave sensor 112. Therefore, wavelength selectivity in electromagnetic-wave sensitivity is improved.

Second Embodiment

Figure 8:
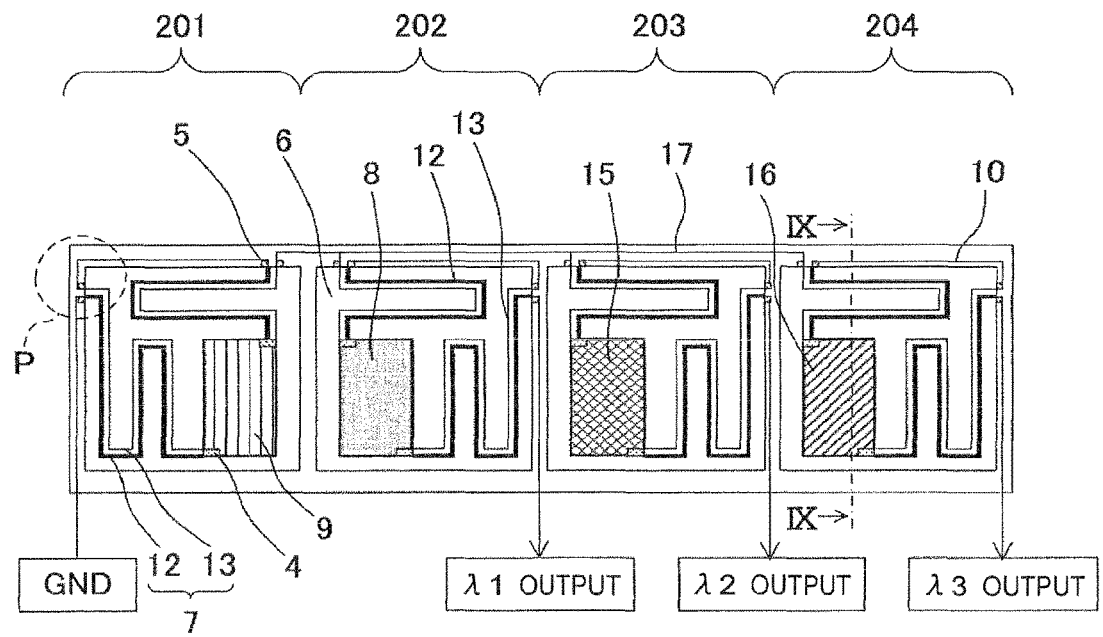
FIG. 8 is a top view of an electromagnetic wave detector according to a second embodiment of the present invention.
Figure 8:
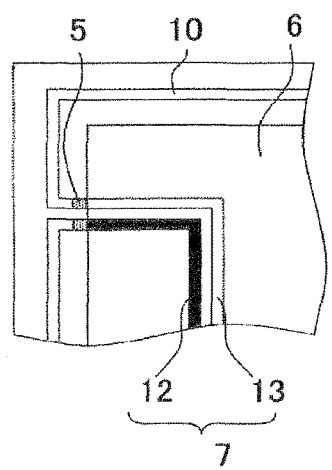
Figure 9:
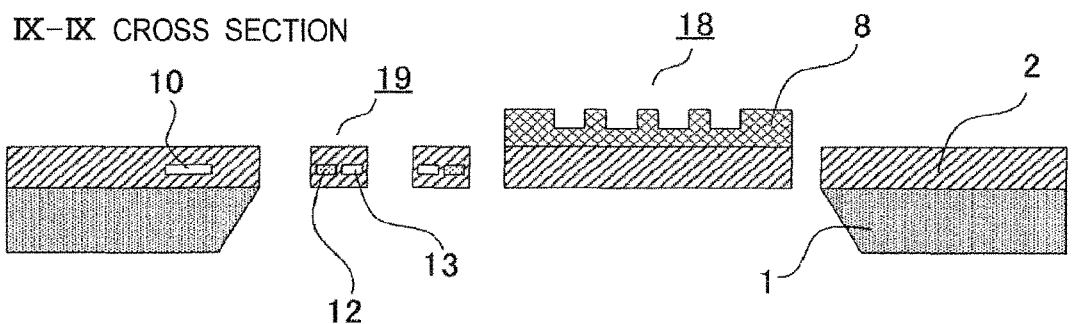
FIG. 9 is a cross-sectional view taken along line IX-IX in FIG. 8(a).

FIG. 8 is a view illustrating a configuration of an electromagnetic wave detector 200 according to a second embodiment of the present invention. FIG. 8(a) is a top view, and FIG. 8(b) is an enlarged view of a portion indicated by dashed circle P in FIG. 8(a). FIG. 9 is a cross-sectional view taken along line IX-IX in FIG. 8(a). Similarly to FIG. 1, in FIG. 8(a), for the sake of easy understanding, an insulating film 2 on a substrate 1 is not illustrated, and electromagnetic wave absorption bodies 8, 15, and 16, and a reflective film 9, which are provided on hot junctions 4, are illustrated in a see-through state. The difference between the electromagnetic wave detector 200 according to the present embodiment and the electromagnetic wave detector 100 according to the first embodiment is that the electromagnetic wave detector 200 of the present embodiment further includes a third electromagnetic wave sensor 203 and a fourth electromagnetic wave sensor 204 each of which detects light in a predetermined wavelength range. The configuration of the electromagnetic wave detector 200 other than the above is identical to the configuration in the first embodiment. Therefore, the configuration specific to the present embodiment will be mainly described. Note that the structure of a support leg 19 according to the present embodiment differs from the structure of the support leg 19 according to the first embodiment; however, the structure of the support leg 19 is not particularly limited as long as structures of the support legs of electromagnetic wave sensors the difference in output between which is calculated are identical. In addition, the expression "structures are identical" includes a case of line symmetric arrangement as in a case of a first electromagnetic wave sensor 201 and a second electromagnetic wave sensor 202 illustrated in FIG. 8(a).

First, the structure of the electromagnetic wave detector 200 according to the present embodiment will be described. As illustrated in the drawing, a plurality of electromagnetic sensors, that is, the first electromagnetic wave sensor 201 including the reflective film 9, the second electromagnetic wave sensor 202, the third electromagnetic wave sensor 203, and the fourth electromagnetic wave sensor 204 each of which detects light in a predetermined wavelength range are arranged to be adjacent to one another on the substrate 1.

A light reception unit 18 of the first electromagnetic wave sensor 201 includes the reflective film 9, and the reflective film 9 is provided to cover hot junctions 4. A light reception unit 18 of the second electromagnetic wave sensor 202 includes an electromagnetic wave absorption body 8 having a detection wavelength range λ1, and the electromagnetic wave absorption body 8 is provided to cover hot junctions 4. A light reception unit 18 of the third electromagnetic wave sensor 203 includes an electromagnetic wave absorption body 15 having a detection wavelength range λ2, and the electromagnetic wave absorption body 15 is provided to cover hot junctions 4. A light reception unit 18 of the fourth electromagnetic wave sensor 204 includes an electromagnetic wave absorption body 16 having a detection wavelength range λ3, and the electromagnetic wave absorption body 16 is provided to cover hot junctions 4.

In the electromagnetic wave absorption bodies 8, 15, and 16, recesses are provided, for example, in an array. The recesses are arranged at equal intervals, and the cycle (pitch) of the recesses is set to be approximately equal to the wavelength of an electromagnetic wave to be detected (specific wavelength). In addition, the depth of the recess is preferably about a quarter of the specific wavelength, which is the wavelength to be detected.

For example, in a case where the specific wavelength to be detected is 5 µm, the shape of the recess is preferably a square (plane) with the side of 3 µm, the depth is preferably 1.5 µm, and the distance between the recesses is preferably 5 µm. In this case, the cycle (pitch) of the recesses is 5 µm, which is equal to the detection wavelength. The plane shape of the recess may be circular.

The first electromagnetic wave sensor 201 including the reflective film 9 provided on the hot junctions 4, and the second, the third, and the fourth electromagnetic wave sensors 202, 203, and 204 including the electromagnetic wave absorption bodies 8, 15, and 16 each of which is provided on the hot junctions 4 and absorb light in a predetermined wavelength band are electrically connected to each other via wiring 17 such that sensor output (thermoelectromotive force) of the first electromagnetic wave sensor 201 is subtracted from the sensor output (thermoelectromotive force) of each of the second, the third, and the fourth electromagnetic wave sensors 202, 203, and 204. In addition, the second, the third, and the fourth electromagnetic wave sensors 202, 203, and 204 share a connection portion between them and the first electromagnetic wave sensor 201. Output of the first electromagnetic wave sensor 201 and sensor output of each of the second, the third, and the fourth electromagnetic wave sensors 202, 203, and 204 are calculated, and signals corresponding to the detection wavelength ranges $\lambda 1$, $\lambda 2$, and $\lambda 3$ are output from an output pad.

As described above, the electromagnetic wave detector 200 according to the present embodiment includes: the first electromagnetic wave sensor 201 which includes the light reception unit 18 held in midair above the substrate 1 by the support leg 19; the second electromagnetic wave sensor 202 which includes the light reception unit 18 held in midair above the substrate 1 by the support leg 19 having the structure identical to that of the support leg 19 of the first electromagnetic wave sensor 201, the second electromagnetic wave sensor 202 being provided to be adjacent to the first electromagnetic wave sensor 201; the third electromagnetic wave sensor 203 which includes the light reception unit 18 held in midair above the substrate 1 by the support leg 19 having the structure identical to that of the support leg 19 of the first electromagnetic wave sensor 201, the third electromagnetic wave sensor 203 being provided to be adjacent to the second electromagnetic wave sensor 202; and the fourth electromagnetic wave sensor 204 which includes the light reception unit 18 held in midair above the substrate 1 by the support leg 19 having the structure identical to that of the support leg 19 of the first electromagnetic wave sensor 201, the fourth electromagnetic wave sensor 204 being provided to be adjacent to the third electromagnetic wave sensor 203. The light reception unit 18 of the first electromagnetic wave sensor 201 includes the reflective film 9. The light reception units 18 of the second electromagnetic wave sensor 202, the third electromagnetic wave sensor 203, and the fourth electromagnetic wave sensor 204 include the electromagnetic wave absorption bodies 8, 15, and 16, respectively. Each of the electromagnetic wave absorption bodies 8, 15, and 16 detects light in predetermined wavelength band different from those of the others or light of predetermined polarization different from those of the others. The difference in output between the first electromagnetic wave sensor 201 and each of the second electromagnetic wave sensor 202, the third electromagnetic wave sensor 203, and the fourth electromagnetic wave sensor 204 is output.

Thus, sensor output caused by electromagnetic wave absorption by the support leg 19 which holds the light reception unit 18 in midair can be subtracted from the output of each of the second electromagnetic wave sensor 202, the third electromagnetic wave sensor 203, and the fourth electromagnetic wave sensor 204, and therefore improved wavelength selectivity in electromagnetic-wave sensitivity in predetermined wavelength bands is achieved by the plurality of electromagnetic wave sensors. In addition, since the connection portion of the wiring 17 is shared by the plurality of sensors, the size of the electromagnetic wave detector 200 can be reduced. Note that in the present embodiment, the configuration where three electromagnetic wave sensors corresponding to the detection wavelength ranges $\lambda 1$, $\lambda 2$, and $\lambda 3$ are provided has been described. However, any configuration may be adopted as long as a plurality of electromagnetic wave sensors each including an electromagnetic wave absorption body 8 which detects light in a predetermined wavelength band is provided. The number of electromagnetic wave sensors is not limited to this.

Third Embodiment

In the first and second embodiments, cases where the electromagnetic wave absorption body 8 detects only light in a specific wavelength band have been described. However, a similar effect can be obtained also in a case where the electromagnetic wave absorption body 8 detects only specific polarized light. That is, even though the electromagnetic wave absorption body 8 itself absorbs and detects specific polarized light, it is not possible to absorb only the specific polarized light by the support leg 19. The reason is as follows. It is not possible to provide the electromagnetic wave absorption body 8 on the support leg 19 formed into an elongated shape so as to increase heat resistance in order to reduce heat escaping from the light reception unit 18 to the substrate 1. Therefore, also in an electromagnetic wave sensor including the electromagnetic wave absorption body 8 which detects only light in a specific polarized light, sensor output includes output caused by absorption by the electromagnetic wave absorption body 8 and output caused by absorption by the support leg 19, and polarization selectivity deteriorates. As described, also in a case of detecting specific polarized light, the technique of eliminating an influence of absorption at the support leg 19 by using the difference in output is effective for improving polarization selectivity.

The structure of an electromagnetic wave absorption body 8 which detects specific polarized light can be realized by changing the shape of the recesses and projections periodically arranged in the light reception unit 18 using surface plasmons described in the first embodiment into an ellipse, a rectangle, or the like. In addition, grooves one-dimensionally and periodically arranged may be possible. In a case where a periodic metal pattern is provided on an incident surface, the shape of the metal pattern may have a highly symmetric shape such as a rectangle or an ellipse.

Alternatively, in a case where the electromagnetic wave absorption body 8 is made of a dielectric multilayer film, polarization selectivity can be realized if the multilayer film of the dielectric has a structure in which projections and recesses are one-dimensionally and periodically formed.

Fourth Embodiment

Figure 10:
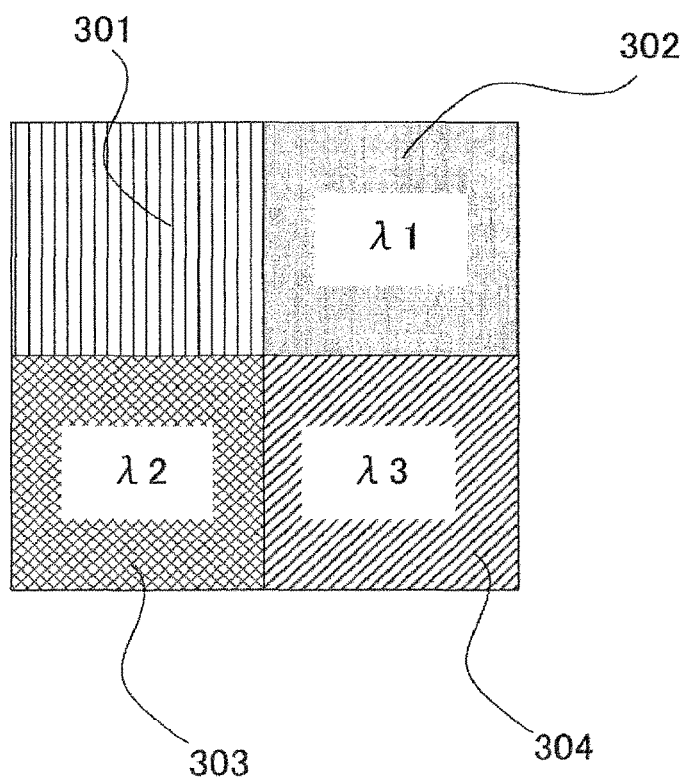
FIG. 10 is a top view of an electromagnetic wave detector according to a fourth embodiment of the present invention.

FIG. 10 is a diagram illustrating a configuration of an electromagnetic wave detector 300 according to a fourth embodiment of the present invention. In the second embodiment, the configuration has been described where the hot junctions 4 are covered with the electromagnetic wave absorption bodies 8, 15, and 16 corresponding to the detection wavelength ranges $\lambda 1$, $\lambda 2$, and $\lambda 3$, respectively, and the plurality of electromagnetic wave sensors, that is, the second, the third, and the fourth electromagnetic wave sensors 202, 203, and 204 each of which detects light in a predetermined wavelength range are arranged to be adjacent to one another one-dimensionally as illustrated in FIG. 8(a). In the electromagnetic wave detector 300 according to the present embodiment as illustrated in FIG. 10, second, third, and fourth electromagnetic wave sensors 302, 303, and 304 each of which detects light in a specific wavelength range are arranged so as to be in contact with a first electromagnetic wave sensor 301 that includes a reflective film 9 provided on hot junctions 4. That is, in the second embodiment, only the second electromagnetic wave sensor 202 is provided to be adjacent to the first electromagnetic wave sensor 201; however, the plurality of electromagnetic wave sensors 302, 303, and 304 may be arranged to be adjacent to the first electromagnetic wave sensor 301 as in the present embodiment.

Thus, since subtraction of sensor output caused by electromagnetic wave absorption by a support leg 19 which holds a light reception unit 18 in midair is possible between adjacent electromagnetic sensors, the length of wiring 17 which connects output of the first electromagnetic wave sensor 301 and output of another electromagnetic wave sensor becomes shorter. As a result, improved wavelength selectivity in electromagnetic-wave sensitivity in arbitrary wavelength bands is achieved by the plurality of electromagnetic wave sensors. In addition, in a case where the electromagnetic wave detectors 300 with the present configuration are arranged in a two-dimensional array, each of the electromagnetic wave sensors 302, 303, and 304 can be arranged at equal pitches.

Fifth Embodiment

A configuration of an electromagnetic wave detector according to a fifth embodiment of the present invention will be described. The present embodiment differs from the first embodiment in a characteristic of a reflective film 9 provided on hot junctions of a first electromagnetic wave sensor.

In the electromagnetic wave detector 100 according to the first embodiment, the reflective film 9 is provided on the hot junctions 4 of the first electromagnetic wave sensor 111. In contrast, in the electromagnetic wave detector according to the present embodiment, the reflective film 9 which reflects light with a wavelength outside a specific wavelength band W1 included in a wavelength band W2 of light detected by an electromagnetic wave absorption body 8 of a second electromagnetic wave sensor 112 is provided on the hot junctions 4. In other words, the reflective film 9 absorbs light with the specific wavelength band W1 included in the wavelength band W2 of light detected by the electromagnetic wave absorption body 8 of the second electromagnetic wave sensor 112, and reflects light with a wavelength other than that. Therefore, sensor output of the first electromagnetic wave sensor 111 includes sensor output (thermoelectromotive force) caused by absorption of the light in the specific wavelength band. The first electromagnetic wave sensor 111 including the reflective film 9 which reflects light with a wavelength outside the specific wavelength band W1 and the second electromagnetic wave sensor 112 including the electromagnetic wave absorption body 8 which absorbs light in the specific wavelength band W2 are electrically connected to each other such that sensor output (thermoelectromotive force) of the first electromagnetic wave sensor 111 is subtracted from the sensor output (thermoelectromotive force) of the second electromagnetic wave sensor 112. Sensor output obtained as a result of subtraction is read as a signal from an output pad 11.

Figure 11:
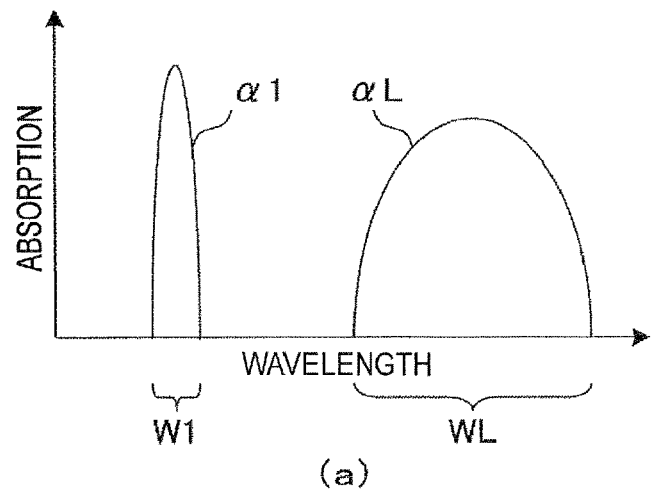
FIG. 11 is a schematic view for illustrating absorption characteristics of an electromagnetic wave detector according to a fifth embodiment of the present invention.
Figure 11:
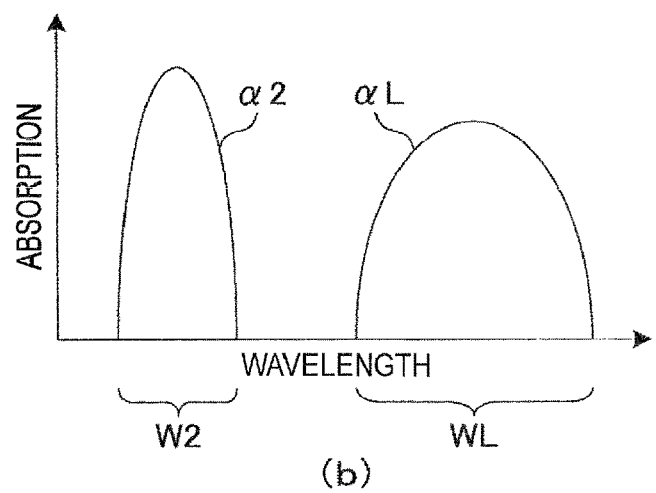
Figure 11:
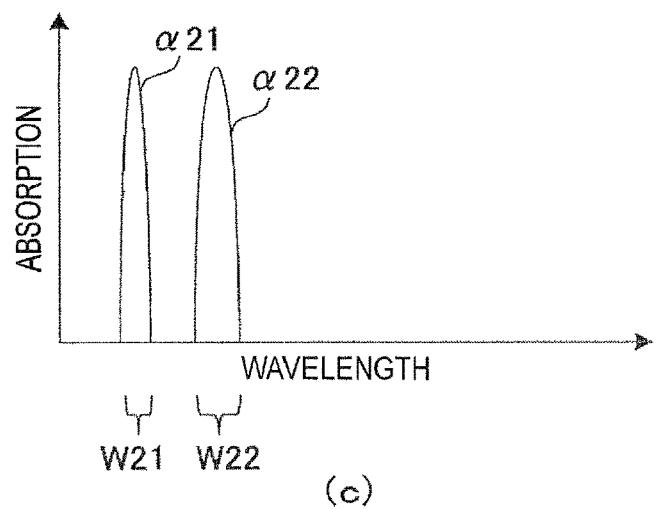

Next, operation of the electromagnetic wave detector according to the fifth embodiment will be described. FIG. 11 is a diagram for illustrating absorption characteristics of the electromagnetic wave detector according to the fifth embodiment of the present invention. FIG. 11(a) illustrates absorption characteristics of the first electromagnetic wave sensor 111. FIG. 11(b) illustrates absorption characteristics of the second electromagnetic wave sensor 112. FIG. 11(c) illustrates absorption characteristics of the electromagnetic wave detector.

As illustrated in FIG. 11(a), in the first electromagnetic wave sensor 111 including the reflective film 9 which detects an electromagnetic wave in the wavelength range W1, absorption α2 by the electromagnetic wave absorption body 8 in the wavelength range W1 and absorption αL by the support leg 19 in the wavelength range WL occur.

In addition, as illustrated in FIG. 11(b), in the second electromagnetic wave sensor 112 including the electromagnetic wave absorption body 8 which detects an electromagnetic wave in the wavelength range W2, absorption α2 by the electromagnetic wave absorption body B in the wavelength range W2 and absorption αL by the support leg 19 in the wavelength range WL occur. Note that the wavelength range W1 is included in the wavelength range W2.

At that time, if the difference in operation between the first electromagnetic wave sensor 111 and the second electromagnetic wave sensor 112 is output, an influence of the absorption αL by the support leg 19 is cancelled, and the final output is the difference between sensor output caused by the absorption α2 by the electromagnetic wave absorption body 8 of the second electromagnetic wave sensor 112 and sensor output caused by the absorption α1 by the reflective film 9 of the first electromagnetic wave sensor 111.

Here, in a case where a full width at half maximum of the absorption α1 and that of the absorption α2 differ from each other, the output of the electromagnetic wave detector according to the present embodiment is obtained from absorption α21 and absorption α22 at two different wavelengths W21 and W22 as illustrated in FIG. 11(c). That is, the electromagnetic wave detector according to the present embodiment has sensitivity to the two wavelengths W21 and W22.

The following structure is considered as the wavelength selection type electromagnetic wave absorption body 8 which selects a wavelength with a different full width at half maximum. For example, in a case of a structure in which projections and recesses are two-dimensionally and periodically arranged, if the ratio between the arrangement cycle of the projections and recesses and the size of the recess is changed, monochromaticity of a resonance wavelength changes. Therefore, it is possible to change the full width at half maximum of the absorption wavelength. In addition, it is also possible to control the full width at half maximum by changing the metal material. For example, since loss in nickel is greater than loss in gold or silver, the full width at half maximum in the case of the electromagnetic wave absorption body 8 made of nickel is greater than that in the case of the electromagnetic wave absorption body 8 made of gold or silver.

As described, by differentially operating the plurality of electromagnetic wave sensors with different detection wavelengths having full widths at half maximum different from each other, absorption by the support leg is eliminated, and a wavelength band, a wavelength, or the like to be selected can be manipulated. This effect is a function necessary for separating a specific absorption wavelength in an analysis of a gas having a plurality of absorption wavelengths. This effect enables the absorption wavelength of a target object to be accurately specified.

The above configuration of the electromagnetic wave detector enables sensor output caused by electromagnetic wave absorption by the support leg 19 which holds the light reception unit 18 in midair and sensor output of light information in an unnecessary wavelength region to be subtracted. Therefore, wavelength selectivity in electromagnetic wave sensitivity is improved.

Sixth Embodiment

Figure 12:
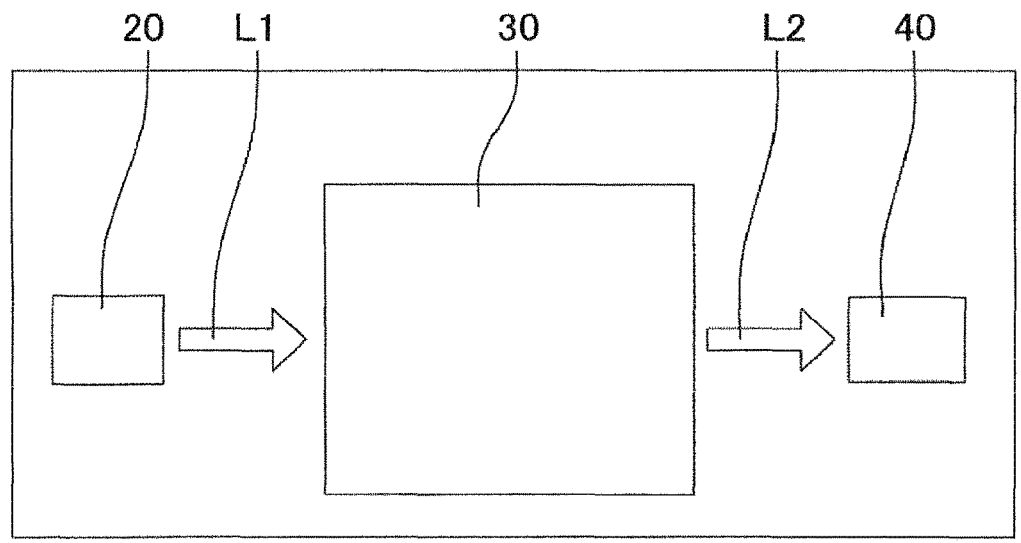
FIG. 12 is a diagram for schematically illustrating a gas analysis device according to a sixth embodiment of the present invention.

A gas analysis device 400 according to a sixth embodiment of the present invention will be described. FIG. 12 is a diagram schematically illustrating a configuration of the gas analysis device 400.

In general, a gas has absorption peaks at a plurality of wavelengths most of which are in the infrared wavelength band. That is, if the absorption peaks of a gas are identified, the kind of the gas can be determined. The gas analysis device 400 according to the present embodiment uses this property of gases to determine the kind of a gas. The gas analysis device 400 includes a light source 20 which emits an electromagnetic wave (infrared ray in the present embodiment), a gas introduction mechanism 30 which introduces a gas to be analyzed, and the electromagnetic wave detector (hereinafter also referred to as a differential infrared sensor array) 40 according to any one of the first to fifth embodiments of the present invention.

The light source 20, the gas introduction mechanism 30, and the differential infrared sensor array 40 are arranged such that an electromagnetic wave L1 emitted from the light source 20 passes through a gas inside the gas introduction mechanism 30, and an electromagnetic wave L2 obtained after the electromagnetic wave L1 has passed through the gas enters the differential infrared sensor array 40. The differential infrared sensor array 40 detects intensity of an electromagnetic wave with a specific wavelength included in the electromagnetic wave L2 having passed through the gas to be analyzed.

The gas introduction mechanism 30 is a container which confines a gas serving as an analysis target. As illustrated in FIG. 12, in a case where the light source 20, the gas introduction mechanism 30, and the differential infrared sensor array 40 are arranged in this order, a window through which the electromagnetic wave L1 emitted from the light source 20 passes and which allows the electromagnetic wave L1 to enter the differential infrared sensor array 40 is provided on the gas introduction mechanism 30. Alternatively, the light source 20 and the differential infrared sensor array 40 may be arranged in the gas introduction mechanism 30.

When the electromagnetic wave L1 passes through the gas enclosed in the gas introduction mechanism 30, the intensity of the electromagnetic wave at the absorption wavelength of the gas attenuates according to the concentration of the gas. Therefore, by setting a plurality of wavelengths which can be detected by the differential infrared sensor array 40, the absorption wavelengths of the gas, that is, the type of the gas can be specified from output of the differential infrared sensor array 40.

The gas analysis device 400 according to the present embodiment can be applied, for example, to a device for detecting carbon dioxide, alcohol in a case of determining an intoxicated state, or the like from a gas serving as an analysis target. In a case where uncooled infrared sensors are used as the differential infrared sensor array 40 of the gas analysis device 400, absorption by the support leg is output. Therefore, it is difficult to perform an accurate analysis. However, according to the present embodiment, an accurate wavelength analysis is made possible.

In addition, it is also possible to mount a plurality of sensors each having a detection wavelength according to a gas species on one device. Therefore, it is possible to realize a gas analysis device with a small and simple configuration.

The above-described electromagnetic wave detector and the gas analysis device which eliminate sensor output caused by absorption by the support leg is also effective in a case where another thermal type electromagnetic wave sensor such as a bolometer, a pyroelectric sensor, or a SOI diode sensor is used.

Seventh Embodiment

Figure 13:
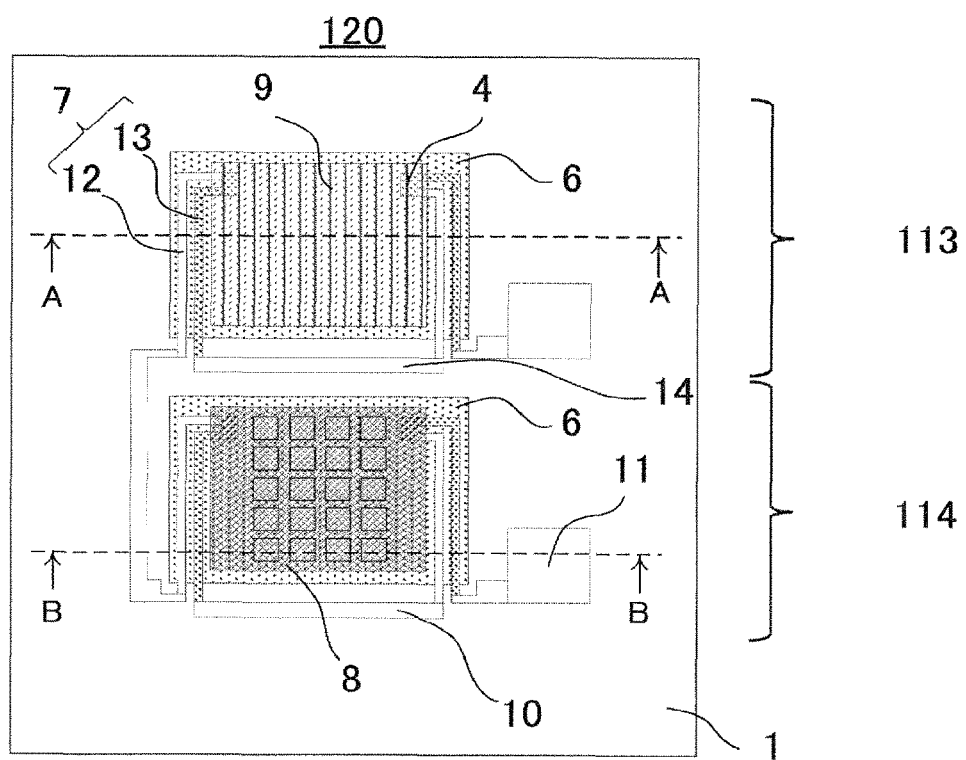
FIG. 13 is a top view of an electromagnetic wave detector according to a seventh embodiment of the present invention.

FIG. 13 is atop view of an electromagnetic wave detector 120 according to a seventh embodiment of the present invention. Each electromagnetic wave sensor includes a substrate 1 made of silicon or the like, a light reception unit 18 which detects an electromagnetic wave by converting the electromagnetic wave into heat, and a support leg (for example, wiring or a thermocouple) 19 which holds the light reception unit (temperature sensor unit) 18 in midair above the substrate 1. An insulating film 2 made of $SiO_2$, SiN, or the like is provided on the surface of the substrate 1. A thermopile (a device including a large number of thermocouples connected in series in order to increase output voltage) 7 including a plurality of thermocouples is provided on the insulating film 2. Output voltage becomes higher as the number of thermocouples is greater. However, as the number of thermocouples is greater, heat escapes more easily from the region of hot junctions 4 to the substrate 1. Here, the insulating film 2 and the thermopile 7 (thermocouples) in the insulating film 2 are collectively referred to as the support leg 19. The support lea 19 has the effect of thermally insulating the light reception unit 18 by holding and floating the light reception unit 18 in midair. By reducing the number of thermocouples and elongating the support leg 19, it is possible to suppress escape of heat from the region of the hot junctions 4 to the substrate 1, and it is possible to provide the highly sensitive electromagnetic wave detector 120.

A configuration of the electromagnetic wave detector 120 according to the seventh embodiment of the present invention will be described. The electromagnetic wave detector 120 includes two electromagnetic sensors described as the underlying technique. Two electromagnetic sensors 113 and 114 differ from each other in the configuration of the light reception unit 18. FIG. 13 is the top view of the electromagnetic wave detector 120 according to the seventh embodiment of the present invention.

Figure 14:
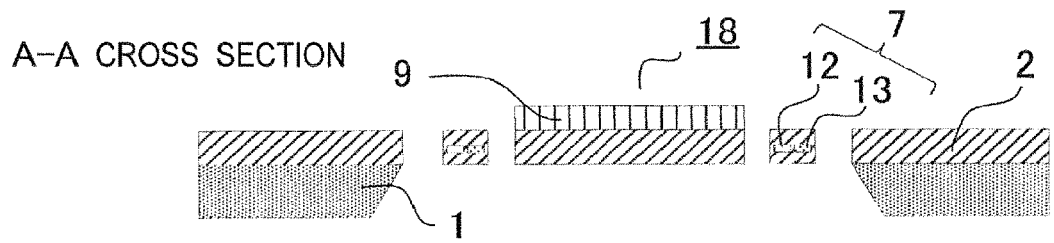
FIG. 14 is a cross-sectional view taken along line A-A in FIG. 13.
Figure 15:
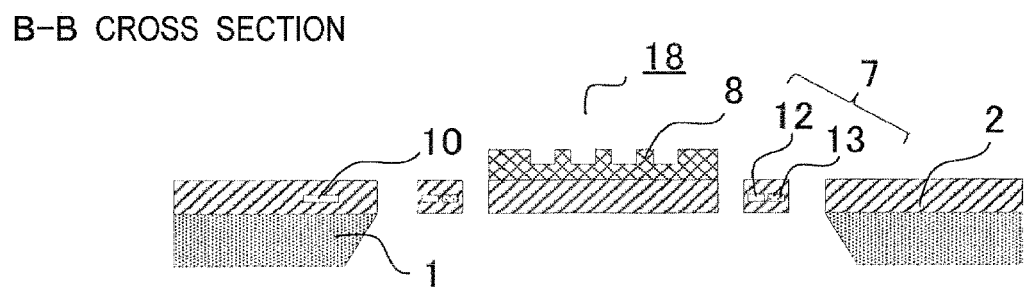
FIG. 15 is a cross-sectional view taken along line B-B in FIG. 13.

FIG. 14 is a cross-sectional view taken along line A-A in FIG. 13. FIG. 15 is a cross-sectional view taken along line B-B in FIG. 13. Similarly to FIG. 1, in FIG. 13, for the sake of easy understanding, the insulating film 2 on the substrate 1 is not illustrated, and an electromagnetic wave absorption body 8 and a reflective film 9 provided on the hot junctions 4 are illustrated in a see-through state.

The electromagnetic wave detector 120 includes the first electromagnetic wave sensor 113 and the second electromagnetic wave sensor 114 arranged to be adjacent to each other on the substrate 1. The first electromagnetic wave sensor 113 and the second electromagnetic wave sensor 114 are connected to each other via wiring 14.

The light reception unit 18 of the first electromagnetic wave sensor 113 includes the reflective film 9, and the reflective film 9 is provided to cover the hot junctions 4 of the thermocouples provided on the insulating film 2. In addition, the light reception unit 18 of the second electromagnetic wave sensor 114 includes the electromagnetic wave absorption body 8 which detects light in a predetermined wavelength band, and the electromagnetic wave absorption body 8 is provided to cover the hot junctions 4. The structures of the first electromagnetic wave sensor 113 and the second electromagnetic wave sensor 114 other than the above are similar to the structure of the electromagnetic wave sensor 110 as the underlying technique described with reference to FIGS. 1 and 2. In addition, the support leg 19 of the first electromagnetic wave sensor 113 and the support leg 19 of the second electromagnetic wave sensor 114 have identical configurations.

The electromagnetic wave detector 120 according to the present embodiment includes the first electromagnetic wave sensor 113 including the reflective film 9 provided on the hot junctions 4, and the second electromagnetic wave sensor 114 including the electromagnetic wave absorption body 8 which is provided on the hot junctions 4 and absorbs light in a predetermined wavelength range. The first electromagnetic wave sensor 113 and the second electromagnetic wave sensor 114 are electrically connected to each other such that sensor output (thermoelectromotive force) of the first electromagnetic wave sensor 113 is subtracted from the sensor output (thermoelectromotive force) of the second electromagnetic wave sensor 114, and a signal is read from an output pad 11. Thus, the electromagnetic wave detector 120 which enables ideal sensor output not including absorption of an electromagnetic wave by the support leg 19 can be realized.

In particular, in the electromagnetic wave detector 120 according to the present embodiment, since the support leg of the first electromagnetic wave sensor 113 and the support leg of the second electromagnetic wave sensor 114 have identical structures, it is possible to eliminate an influence of the electromagnetic wave absorbed by the support leg 19 on sensor output by subtracting sensor output of the first electromagnetic wave sensor 113 from sensor output of the second electromagnetic wave sensor 114.

Figure 16:
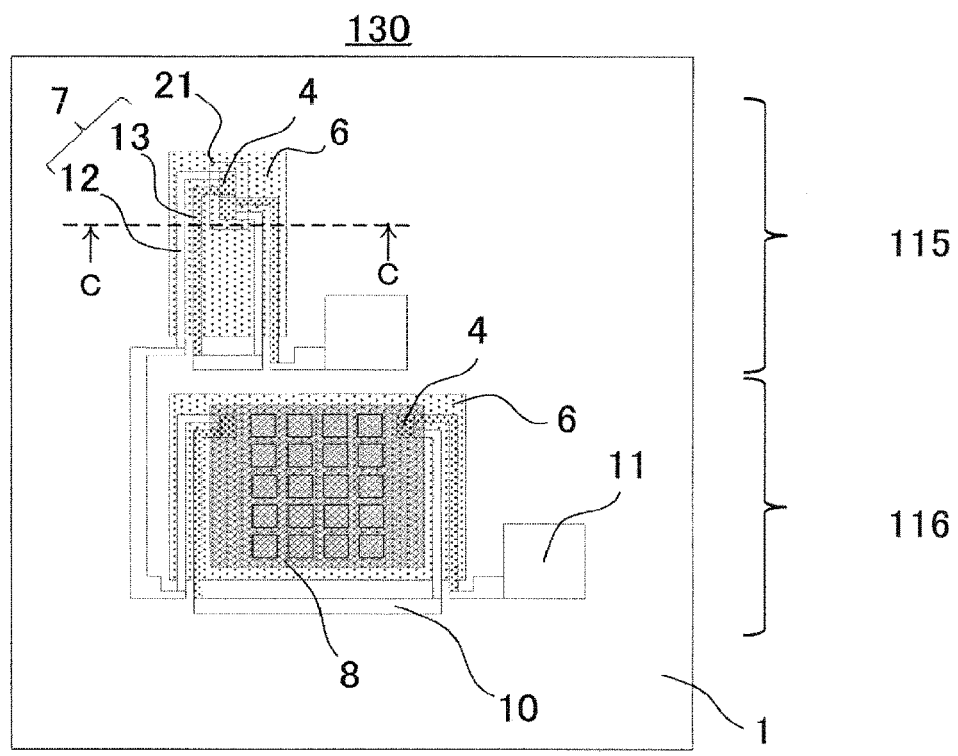
FIG. 16 is atop view of an electromagnetic wave detector according to the seventh embodiment of the present invention.

Sensor output of the first electromagnetic wave sensor 113 requires only absorption by the support leg 19. Therefore, also in an electromagnetic wave detector 130 including a fifth electromagnetic wave sensor 115 which does not include a light reception unit 18 and a second electromagnetic wave sensor 116 which includes an electromagnetic wave absorption body 8 that absorbs light in a predetermined wavelength range as illustrated in FIG. 16, ideal sensor output not including absorption of an electromagnetic wave by a support leg 19 can be obtained. Thus, the size of the electromagnetic wave detector can be reduced.

Figure 17:
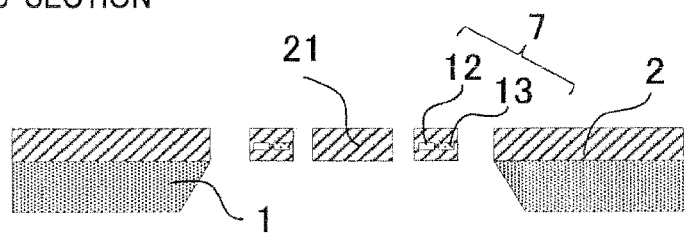
FIG. 17 is an example of a cross-sectional view taken along line C-C in FIG. 16.

As described, the electromagnetic wave detector 130 according to the present embodiment includes the fifth electromagnetic wave sensor 115 in which the support leg 19 is held in midair above a substrate 1, and the second electromagnetic wave sensor 116 which includes an light reception unit 18 held in midair above a substrate 1 by the support leg 19 which has a structure identical to that of the support leg 19 of the fifth electromagnetic wave sensor 115 and provided to be adjacent to the fifth electromagnetic wave sensor 115. The fifth electromagnetic wave sensor 115 does not include a light reception unit 18. As illustrated in a cross-sectional view in FIG. 17 taken along line C-C in FIG. 16, hot junctions 4 of thermocouples are thermally connected at a hot junction region 21 made of an insulating film 2, and the light reception unit 18 of the second electromagnetic wave sensor 116 includes the electromagnetic wave absorption body 8 which detects light in a predetermined wavelength band or light of a predetermined polarization. The difference between output of the second electromagnetic wave sensor 116 and output of the fifth electromagnetic wave sensor 115 is output. Here, the insulating film 2 in the hot junction region 21 may not be included.

Figure 18:
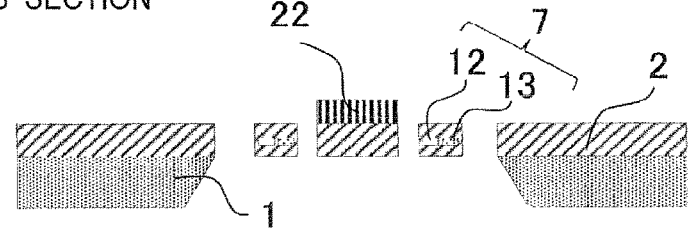
FIG. 18 is an example of the cross-sectional view taken along line C-C in FIG. 16.

In addition, as illustrated in a cross-sectional view in FIG. 18 taken along line C-C in FIG. 16, a reflective film 22 made of a material having large specific heat may be formed in the hot junction region 21 in order to adjust temperature distribution in the support leg 19 due to electromagnetic wave absorption by the support leg 19.

According to the above configuration, sensor output caused by electromagnetic wave absorption by the support leg 19 which holds the light reception unit 18 in midair can be subtracted from output of the second electromagnetic wave sensor 116. Therefore, wavelength selectivity in electromagnetic-wave sensitivity is improved.

Eighth Embodiment

Figure 19:
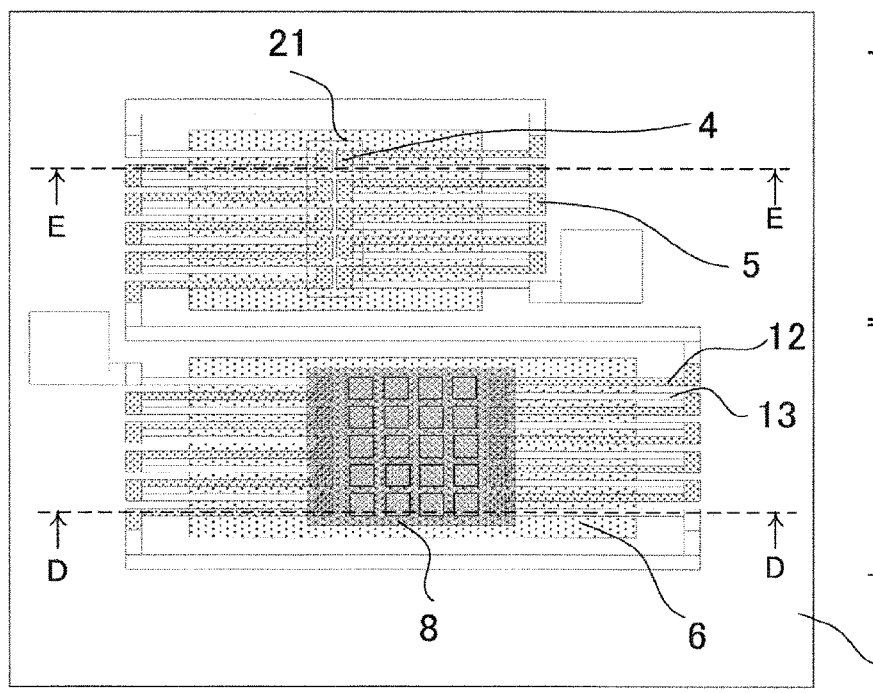
FIG. 19 is a top view of an electromagnetic wave detector according to an eighth embodiment of the present invention.
Figure 20:
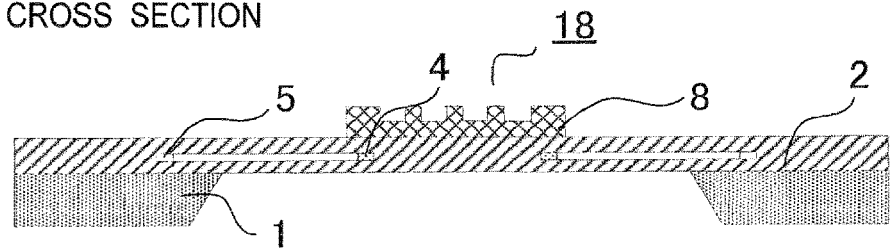
FIG. 20 is a cross-sectional view taken along line D-D in FIG. 19.
Figure 21:
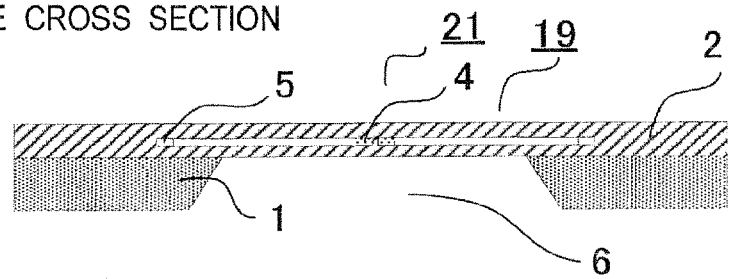
FIG. 21 is a cross-sectional view taken along line E-E in FIG. 19.

FIG. 19 is a top view of an electromagnetic wave detector 140 according to an eighth embodiment of the present invention. FIG. 20 is a cross-sectional view taken along line D-D in FIG. 19. In addition, FIG. 21 is a cross-sectional view taken along line E-E in FIG. 19. Similarly to FIG. 1, in FIG. 19, for the sake of easy understanding, an insulating film 2 on a substrate 1 is not illustrated, and an electromagnetic wave absorption body 8 provided on hot junctions 4 is illustrated in a see-through state.

The difference from the seventh embodiment is that thermopiles (a device including a large number of thermocouples connected in series in order to increase output voltage) 7 including a plurality of thermocouples are provided on the insulating films 2 of a fifth electromagnetic wave sensor 117 and a second electromagnetic wave sensor 118 arranged to be adjacent to each other on the substrate 1. Output voltage becomes higher as the number of thermocouples is greater.

Ninth Embodiment

Figure 22:
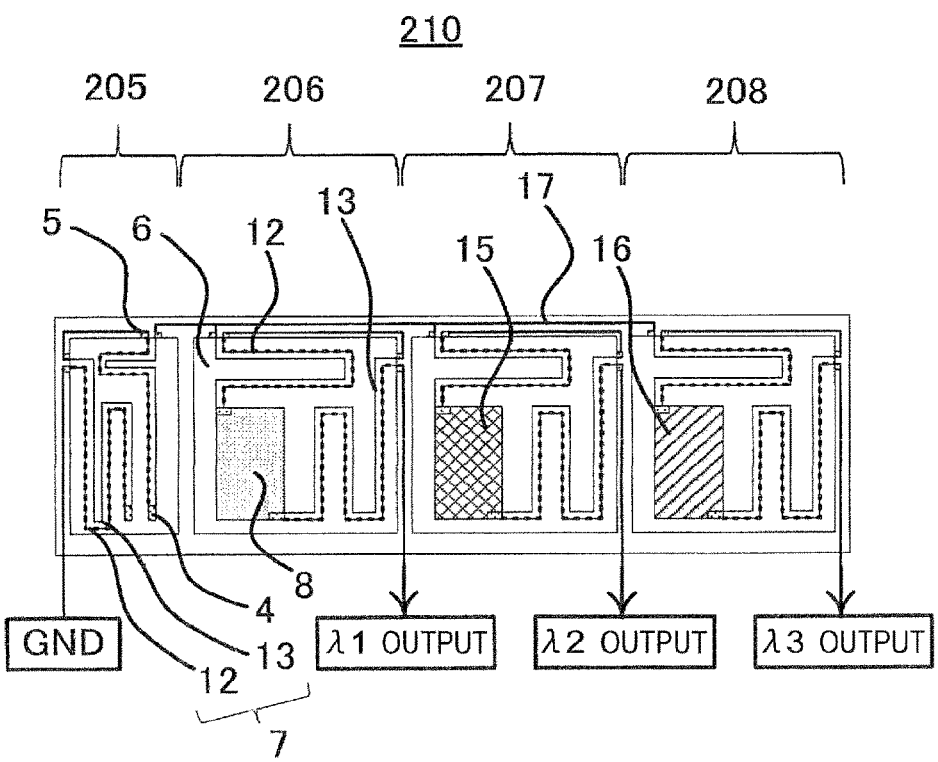
FIG. 22 is a top view of an electromagnetic wave detector according to a ninth embodiment of the present invention.

FIG. 22 is a diagram illustrating a configuration of an electromagnetic wave detector 210 according to a ninth embodiment of the present invention. Similarly to FIG. 1, in FIG. 22, for the sake of easy understanding, an insulating film 2 on a substrate 1 is not illustrated, and electromagnetic wave absorption bodies 8, 15, and 16 provided on hot junctions 4 are illustrated in a see-through state. The electromagnetic wave detector 210 according to the present embodiment differs from the electromagnetic wave detector 120 according to the seventh embodiment in that the electromagnetic wave detector 210 further includes a third electromagnetic wave sensor 207 and a fourth electromagnetic wave sensor 208 each of which detects light in a predetermined wavelength range. The configuration other than the above is identical to that in the seventh embodiment. Therefore, the configuration specific to the present embodiment will be mainly described below.

The structure of a support leg 19 according to the present embodiment differs from the structure of the support leg 19 according to the seventh embodiment. However, the structure of the support leg 19 is not particularly limited as long as structures, widths, and lengths of the support legs of electromagnetic wave sensors the difference in output between which is calculated are identical.

First, the structure of the electromagnetic wave detector 210 according to the present embodiment will be described. As illustrated in the drawing, a plurality of electromagnetic sensors, that is, a fifth electromagnetic wave sensor 205 which does not include a light reception unit 18, a second electromagnetic wave sensor 206, the third electromagnetic wave sensor 207, and the fourth electromagnetic wave sensor 208 each of which detects light in a predetermined wavelength range are arranged to be adjacent to one another on the substrate 1.

The fifth electromagnetic wave sensor 205 does not include a light reception unit 18. A light reception unit 18 of the second electromagnetic wave sensor 206 includes an electromagnetic wave absorption body 8 having a detection wavelength range $\lambda 1$, and the electromagnetic wave absorption body 8 is provided to cover hot junctions 4. A light reception unit 18 of the third electromagnetic wave sensor 207 includes an electromagnetic wave absorption body 15 having a detection wavelength range $\lambda 2$, and the electromagnetic wave absorption body 15 is provided to cover hot junctions 4. A light reception unit 18 of the fourth electromagnetic wave sensor 208 includes an electromagnetic wave absorption body 16 having a detection wavelength range $\lambda 3$, and the electromagnetic wave absorption body 16 is provided to cover hot junctions 4.

The electromagnetic wave detector 210 according to the present embodiment includes: the fifth electromagnetic wave sensor 205 configured only of the support lea 19; the second electromagnetic wave sensor 206 which includes the light reception unit 18 held in midair above the substrate 1 by the support leg 19 that has the structure identical to that of the support leg 19 of the fifth electromagnetic wave sensor 205, the second electromagnetic wave sensor 206 being provided to be adjacent to the fifth electromagnetic wave sensor 205; the third electromagnetic wave sensor 207 which includes the light reception unit 18 held in midair above the substrate 1 by the support leg 19 which has the structure identical to that of the support leg 19 of the fifth electromagnetic wave sensor 205, the third electromagnetic wave sensor 207 being provided to be adjacent to the second electromagnetic wave sensor 206; and the fourth electromagnetic wave sensor 208 which includes the light reception unit 18 held in midair above the substrate 1 by the support leg 19 which has the structure identical to that of the support leg 19 of the fifth electromagnetic wave sensor 205, the fourth electromagnetic wave sensor 208 being provided to be adjacent to the third electromagnetic wave sensor 207. The light reception units of the second electromagnetic wave sensor 206, the third electromagnetic wave sensor 207, and the fourth electromagnetic wave sensor 208 include the electromagnetic wave absorption bodies 8, 15 and 16 which detect light in predetermined wavelength bands or lights of predetermined polarizations, the wavelength bands and the polarizations from one another. The difference between output of the fifth electromagnetic wave sensor 205 and output of each of the second electromagnetic wave sensor 206, the third electromagnetic wave sensor 207, and the fourth electromagnetic wave sensor 208 is output.

Thus, sensor output caused by electromagnetic wave absorption by the support leg 19 can be subtracted from the output of each of the second electromagnetic wave sensor 206, the third electromagnetic wave sensor 207, and the fourth electromagnetic wave sensor 208, and therefore improved wavelength selectivity in electromagnetic-wave sensitivity in predetermined wavelength bands is achieved by the plurality of electromagnetic wave sensors. In addition, since a connection portion of wiring 17 is shared by the plurality of sensors, the size of the electromagnetic wave detector 210 can be reduced. Note that in the present embodiment, the configuration where three electromagnetic wave sensors corresponding to the detection wavelength ranges $\lambda 1$, $\lambda 2$, and $\lambda 3$ are provided has been described. However, any configuration may be adopted as long as a plurality of electromagnetic wave sensors each including an electromagnetic wave absorption body 8 which detects light in a predetermined wavelength band is provided. The number of electromagnetic wave sensors is not limited to this.

DESCRIPTION OF REFERENCE SYMBOLS

1 SUBSTRATE
2 INSULATING FILM
3 ELECTROMAGNETIC WAVE ABSORPTION BODY
4 HOT JUNCTION
5 COLD JUNCTION
6 CAVITY
7 THERMOPILE
8 ELECTROMAGNETIC WAVE ABSORPTION BODY
9 REFLECTIVE FILM
10 WIRING
11 OUTPUT PAD
12 THERMOCOUPLE MATERIAL a
13 THERMOCOUPLE MATERIAL b
14 WIRING
15 ELECTROMAGNETIC WAVE ABSORPTION BODY
16 ELECTROMAGNETIC WAVE ABSORPTION BODY
17 WIRING
18 LIGHT RECEPTION UNIT
19 SUPPORT LEG
20 LIGHT SOURCE
21 HOT JUNCTION REGION
22 REFLECTIVE FILM
30 GAS INTRODUCTION MECHANISM
40 DIFFERENTIAL INFRARED SENSOR ARRAY
100 ELECTROMAGNETIC WAVE DETECTOR
110 ELECTROMAGNETIC WAVE SENSOR
111 FIRST ELECTROMAGNETIC WAVE SENSOR
112 SECOND ELECTROMAGNETIC WAVE SENSOR
113 FIRST ELECTROMAGNETIC WAVE SENSOR
114 SECOND ELECTROMAGNETIC WAVE SENSOR
115 FIFTH ELECTROMAGNETIC WAVE SENSOR
116 SECOND ELECTROMAGNETIC WAVE SENSOR
117 FIFTH ELECTROMAGNETIC WAVE SENSOR
118 SECOND ELECTROMAGNETIC WAVE SENSOR
120 ELECTROMAGNETIC WAVE DETECTOR
130 ELECTROMAGNETIC WAVE DETECTOR
140 ELECTROMAGNETIC WAVE DETECTOR
200 ELECTROMAGNETIC WAVE DETECTOR
201 FIRST ELECTROMAGNETIC WAVE SENSOR
202 SECOND ELECTROMAGNETIC WAVE SENSOR
203 THIRD ELECTROMAGNETIC WAVE SENSOR
204 FOURTH ELECTROMAGNETIC WAVE SENSOR
205 FIFTH ELECTROMAGNETIC WAVE SENSOR
206 SECOND ELECTROMAGNETIC WAVE SENSOR
207 THIRD ELECTROMAGNETIC WAVE SENSOR
208 FOURTH ELECTROMAGNETIC WAVE SENSOR
210 ELECTROMAGNETIC WAVE DETECTOR
300 ELECTROMAGNETIC WAVE DETECTOR
301 FIRST ELECTROMAGNETIC WAVE SENSOR

302 SECOND ELECTROMAGNETIC WAVE SENSOR
303 THIRD ELECTROMAGNETIC WAVE SENSOR
304 FOURTH ELECTROMAGNETIC WAVE SENSOR
400 GAS ANALYSIS DEVICE

The invention claimed is:

1. An electromagnetic wave detector comprising:
a substrate;
a first electromagnetic wave sensor configured to include a light reception unit which is held in midair above the substrate by a support leg; and
a second electromagnetic wave sensor configured to include a light reception unit which is held in midair above the substrate by a support leg that has a structure identical to a structure of the support leg of the first electromagnetic wave detector, the second electromagnetic wave sensor being provided to be adjacent to the first electromagnetic wave sensor, wherein
the light reception unit of the first electromagnetic wave sensor is formed on the same plane as the support leg and includes a flat reflective film which covers an entire surface of the light reception unit,
the light reception unit of the second electromagnetic wave sensor is formed on the same plane as the support leg and includes an electromagnetic wave absorption body which detects one of light in a predetermined wavelength band and light of a predetermined polarization,
the first electromagnetic wave sensor includes the light reception unit comprising the reflective film and the support leg which the electromagnetic wave enters directly, and has the same output as the sensor output caused by the electromagnetic wave absorbed in the area other than the light reception unit of the second electromagnetic wave sensor and
a difference between output of the second electromagnetic wave sensor and output of the first electromagnetic wave sensor is output.

2. The electromagnetic wave detector according to claim 1, wherein a surface of the support leg of the first electromagnetic wave sensor and a surface of the support leg of the second electromagnetic wave sensor are exposed.

3. The electromagnetic wave detector according to claim 1, further comprising a third electromagnetic wave sensor configured to include a light reception unit which is held in midair above the substrate by a support leg that has a structure identical to the structure of the support leg of the first electromagnetic wave detector, the third electromagnetic wave sensor being provided to be adjacent to one of the first electromagnetic wave sensor and the second electromagnetic wave sensor, wherein
the light reception unit of the third electromagnetic wave sensor includes an electromagnetic wave absorption body which detects one of light in a wavelength band and light of a polarization, the wavelength band and the polarization differing from the wavelength band and the polarization of the light detected by the electromagnetic wave absorption body of the second electromagnetic wave sensor, and
a difference between output of the third electromagnetic wave sensor and output of the first electromagnetic wave sensor is output.

4. The electromagnetic wave detector according to claim 2, further comprising a third electromagnetic wave sensor configured to include a light reception unit which is held in midair above the substrate by a support leg that has a structure identical to the structure of the support leg of the first electromagnetic wave detector, the third electromagnetic wave sensor being provided to be adjacent to one of the first electromagnetic wave sensor and the second electromagnetic wave sensor, wherein
the light reception unit of the third electromagnetic wave sensor includes an electromagnetic wave absorption body which detects one of light in a wavelength band and light of a polarization, the wavelength band and the polarization differing from the wavelength band and the polarization of the light detected by the electromagnetic wave absorption body of the second electromagnetic wave sensor, and
a difference between output of the third electromagnetic wave sensor and output of the first electromagnetic wave sensor is output.

5. The electromagnetic wave detector according to claim 1, wherein the support leg comprises a thermocouple.

6. The electromagnetic wave detector according to claim 3, wherein
output of the first electromagnetic wave sensor and output of the second electromagnetic wave sensor are electrically connected to each other such that the output of the first electromagnetic wave sensor is subtracted from the output of the second electromagnetic wave sensor,
output of the first electromagnetic wave sensor and output of the third electromagnetic wave sensor are electrically connected to each other such that the output of the first electromagnetic wave sensor is subtracted from the output of the third electromagnetic wave sensor, and
a connection portion between the first electromagnetic wave sensor and the second electromagnetic wave sensor also serves as a connection portion between the first electromagnetic wave sensor and the third electromagnetic wave sensor.

7. The electromagnetic wave detector according to claim 4, wherein
output of the first electromagnetic wave sensor and output of the second electromagnetic wave sensor are electrically connected to each other such that the output of the first electromagnetic wave sensor is subtracted from the output of the second electromagnetic wave sensor,
output of the first electromagnetic wave sensor and output of the third electromagnetic wave sensor are electrically connected to each other such that the output of the first electromagnetic wave sensor is subtracted from the output of the third electromagnetic wave sensor, and
a connection portion between the first electromagnetic wave sensor and the second electromagnetic wave sensor also serves as a connection portion between the first electromagnetic wave sensor and the third electromagnetic wave sensor.

8. The electromagnetic wave detector according to claim 1, wherein the electromagnetic wave absorption body has one of a single-layer structure of a metal film and a multilayer film structure of a metal film and a dielectric.

9. The electromagnetic wave detector according claim 1, wherein the electromagnetic wave absorption body has a periodic structure arranged in an array on a surface of the electromagnetic wave absorption body such that a surface plasmon which causes a specific wavelength to be coupled to the surface is induced, and an absorption amount of incident light with the specific wavelength is made greater than an absorption amount of incident light with a wavelength other than the specific wavelength.

10. The electromagnetic wave detector according to claim 1, wherein the reflective film of the first electromagnetic wave sensor reflects light with a wavelength other than a specific wavelength included in the wavelength band of the light detected by the electromagnetic wave absorption body of the second electromagnetic wave sensor.

11. The electromagnetic wave detector according to claim 1, wherein the reflective film of the first electromagnetic wave sensor is made of a material which has large specific heat.

12. An electromagnetic wave detector comprising:
a substrate;
a fifth electromagnetic wave sensor configured to include a support leg which is held in midair above the substrate; and
a second electromagnetic wave sensor configured to include a light reception unit which is held in midair above the substrate by a support leg that has a structure identical to a structure of the support leg of the fifth electromagnetic wave sensor, the second electromagnetic wave sensor being provided to be adjacent to the fifth electromagnetic wave sensor, wherein
the fifth electromagnetic wave sensor is constituted of only the support leg which is held in midair and the electromagnetic wave enters directly, and the support leg includes a reflective film which is formed on the same plane as the support leg and is provided only on a hot junction region where a hot junction of thermocouple is thermally connected,
the light reception unit of the second electromagnetic wave sensor includes an electromagnetic wave absorption body which detects one of light in a predetermined wavelength band and light of a predetermined polarization, and
a difference between output of the second electromagnetic wave sensor and output of the fifth electromagnetic wave sensor is output.

13. The electromagnetic wave detector according to claim 12, wherein a surface of the support leg of the fifth electromagnetic wave sensor and a surface of the support leg of the second electromagnetic wave sensor are exposed.

14. The electromagnetic wave detector according to claim 12, further comprising a third electromagnetic wave sensor configured to include a light reception unit which is held in midair above the substrate by a support leg that has a structure identical to the structure of the support leg of the fifth electromagnetic wave sensor, the third electromagnetic wave sensor being provided to be adjacent to one of the fifth electromagnetic wave sensor and the second electromagnetic wave sensor, wherein
the fifth electromagnetic wave sensor does not include a light reception unit, and
the light reception unit of the third electromagnetic wave sensor includes an electromagnetic wave absorption body which detects one of light in a wavelength band and light of a predetermined polarization, the wavelength band and the polarization differing from the wavelength band and the polarization of the light detected by the electromagnetic wave absorption body of the second electromagnetic wave sensor, and
a difference between output of the third electromagnetic wave sensor and output of the fifth electromagnetic wave sensor is output.

15. The electromagnetic wave detector according to claim 13, further comprising a third electromagnetic wave sensor configured to include a light reception unit which is held in midair above the substrate by a support leg that has a structure identical to the structure of the support leg of the fifth electromagnetic wave sensor, the third electromagnetic wave sensor being provided to be adjacent to one of the fifth electromagnetic wave sensor and the second electromagnetic wave sensor, wherein
the fifth electromagnetic wave sensor does not include a light reception unit, and
the light reception unit of the third electromagnetic wave sensor includes an electromagnetic wave absorption body which detects one of light in a wavelength band and light of a predetermined polarization, the wavelength band and the polarization differing from the wavelength band and the polarization of the light detected by the electromagnetic wave absorption body of the second electromagnetic wave sensor, and
a difference between output of the third electromagnetic wave sensor and output of the fifth electromagnetic wave sensor is output.

16. The electromagnetic wave detector according to claim 14, wherein
output of the fifth electromagnetic wave sensor and output of the second electromagnetic wave sensor are electrically connected to each other such that the output of the fifth electromagnetic wave sensor is subtracted from the output of the second electromagnetic wave sensor,
output of the fifth electromagnetic wave sensor and output of the third electromagnetic wave sensor are electrically connected to each other such that the output of the fifth electromagnetic wave sensor is subtracted from the output of the third electromagnetic wave sensor, and
a connection portion between the fifth electromagnetic wave sensor and the second electromagnetic wave sensor also serves as a connection portion between the fifth electromagnetic wave sensor and the third electromagnetic wave sensor.

17. The electromagnetic wave detector according to claim 15, wherein
output of the fifth electromagnetic wave sensor and output of the second electromagnetic wave sensor are electrically connected to each other such that the output of the fifth electromagnetic wave sensor is subtracted from the output of the second electromagnetic wave sensor,
output of the fifth electromagnetic wave sensor and output of the third electromagnetic wave sensor are electrically connected to each other such that the output of the fifth electromagnetic wave sensor is subtracted from the output of the third electromagnetic wave sensor, and
a connection portion between the fifth electromagnetic wave sensor and the second electromagnetic wave sensor also serves as a connection portion between the fifth electromagnetic wave sensor and the third electromagnetic wave sensor.

18. A gas analysis device comprising:
the electromagnetic wave detector according to claim 1;
a gas introduction mechanism configured to introduce a gas to be analyzed; and
a light source configured to irradiate the gas to be analyzed with an electromagnetic wave, wherein
intensity of an electromagnetic wave with a specific wavelength included in the electromagnetic wave which has passed through the gas to be analyzed is detected by the electromagnetic wave detector.

19. The gas analysis device according to claim 18, wherein the specific wavelength detected by the electromagnetic wave detector is a wavelength for determining presence of alcohol.

* * * * *